United States Patent
Pi

(10) Patent No.: US 10,410,507 B2
(45) Date of Patent: Sep. 10, 2019

(54) METHOD AND SYSTEM FOR HAND WASHING COMPLIANCE

(71) Applicant: Konrad David Pi, Louiseville, CO (US)

(72) Inventor: Konrad David Pi, Louiseville, CO (US)

( * ) Notice: Subject to any disclaimer, the term of this patent is extended or adjusted under 35 U.S.C. 154(b) by 0 days.

(21) Appl. No.: 15/579,003

(22) PCT Filed: Apr. 8, 2016

(86) PCT No.: PCT/US2016/026711
§ 371 (c)(1),
(2) Date: Dec. 1, 2017

(87) PCT Pub. No.: WO2016/168082
PCT Pub. Date: Oct. 20, 2016

(65) Prior Publication Data
US 2018/0151054 A1 May 31, 2018

(30) Foreign Application Priority Data

Apr. 13, 2015 (CN) .......................... 2015 1 0173233

(51) Int. Cl.
*G08B 21/24* (2006.01)
*G16H 40/20* (2018.01)

(52) U.S. Cl.
CPC .......... *G08B 21/245* (2013.01); *G16H 40/20* (2018.01)

(58) Field of Classification Search
CPC ............................. G08B 21/245; G16H 40/20
USPC ........................................................ 340/573.1
See application file for complete search history.

(56) References Cited

U.S. PATENT DOCUMENTS

| | | | |
|---|---|---|---|
| 8,407,827 B1* | 4/2013 | Friedman | E03C 1/186 4/623 |
| 9,613,518 B2* | 4/2017 | Dunn | G06K 9/00335 |
| 9,721,452 B2* | 8/2017 | Felch | G16H 40/20 |
| 2002/0019709 A1* | 2/2002 | Segal | G07C 1/10 702/45 |
| 2002/0044058 A1* | 4/2002 | Heinrich | G06K 7/0008 340/572.1 |
| 2005/0082503 A1* | 4/2005 | Patterson | G06Q 20/327 251/129.04 |

(Continued)

*Primary Examiner* — Hirdepal Singh

(57) ABSTRACT

A method and system for user hand washing compliance is described. An exemplary embodiment of the method may comprise the steps of: receiving a request from a user to enter a hand-washing-compliance-area, wherein the request is received by an entry-sensor; the entry-sensor may cause initiation of a hand-washing-cycle log entry; releasing water from a washer for pre-rinsing hands of the user; releasing soap from a soap-dispenser for soaping the hands of the user; releasing water from the washer to rinse the soaped hands of the user; and providing a means-to-dry-hands from a hand-dryer for drying the hands of the user. The user may initiate each step with a user-transmitter based on physical proximity and/or by appropriate hand-gestures before a gesture-recognition-camera. Upon the user initiating each step, the gesture-recognition-camera optionally records each step. And at least one server may receive said recordings and validate each step as compliant or non-compliant.

1 Claim, 13 Drawing Sheets

(56) References Cited

U.S. PATENT DOCUMENTS

| | | | | |
|---|---|---|---|---|
| 2007/0173727 | A1* | 7/2007 | Naghavi | A61B 5/01 600/483 |
| 2009/0189981 | A1* | 7/2009 | Siann | H04N 7/183 348/143 |
| 2011/0291841 | A1* | 12/2011 | Hollock | G08B 21/245 340/573.1 |
| 2011/0316703 | A1* | 12/2011 | Butler | G08B 21/245 340/573.1 |
| 2012/0062382 | A1* | 3/2012 | Taneff | G08B 21/245 340/573.1 |
| 2012/0146903 | A1* | 6/2012 | Arihara | G06F 3/011 345/158 |
| 2015/0022361 | A1* | 1/2015 | Gaisser | G08B 21/245 340/573.1 |
| 2015/0077258 | A1* | 3/2015 | Nelson | G08B 21/245 340/573.1 |
| 2015/0216369 | A1* | 8/2015 | Hamilton | A47K 5/1217 222/1 |
| 2015/0302769 | A1* | 10/2015 | Johnson | G09B 19/0076 434/308 |
| 2017/0256155 | A1* | 9/2017 | Sengstaken, Jr. | G06K 7/10009 |

\* cited by examiner

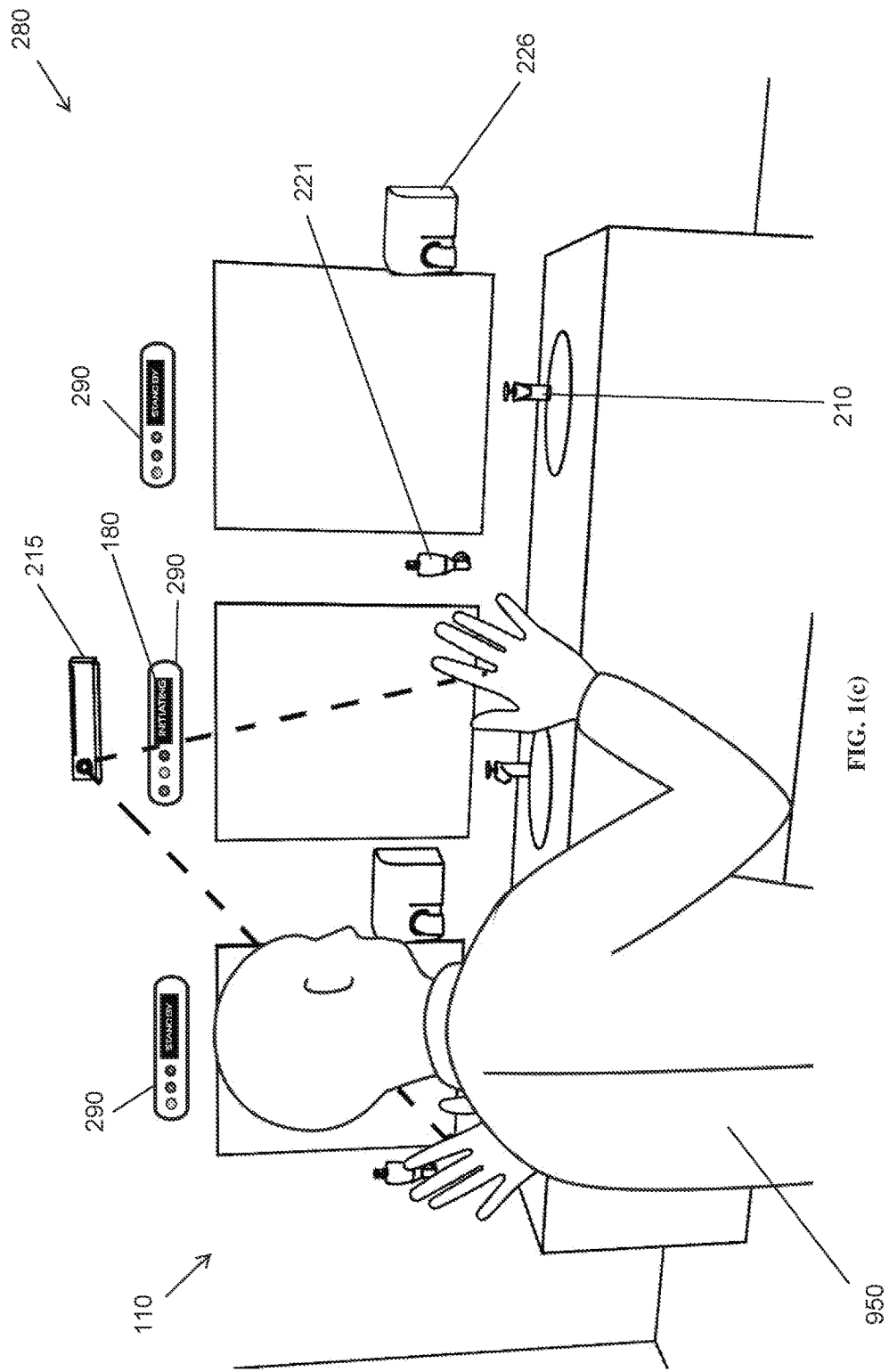

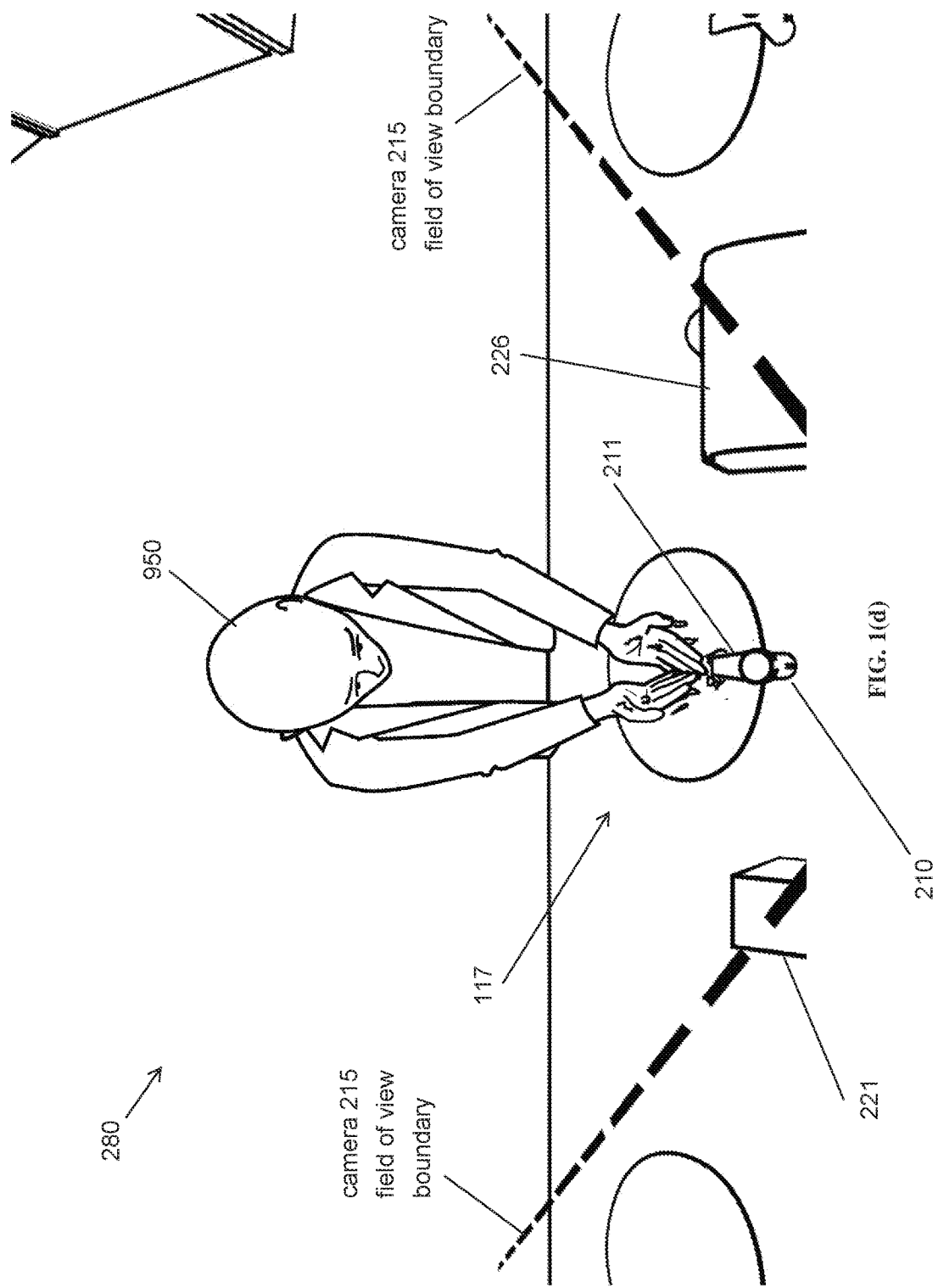

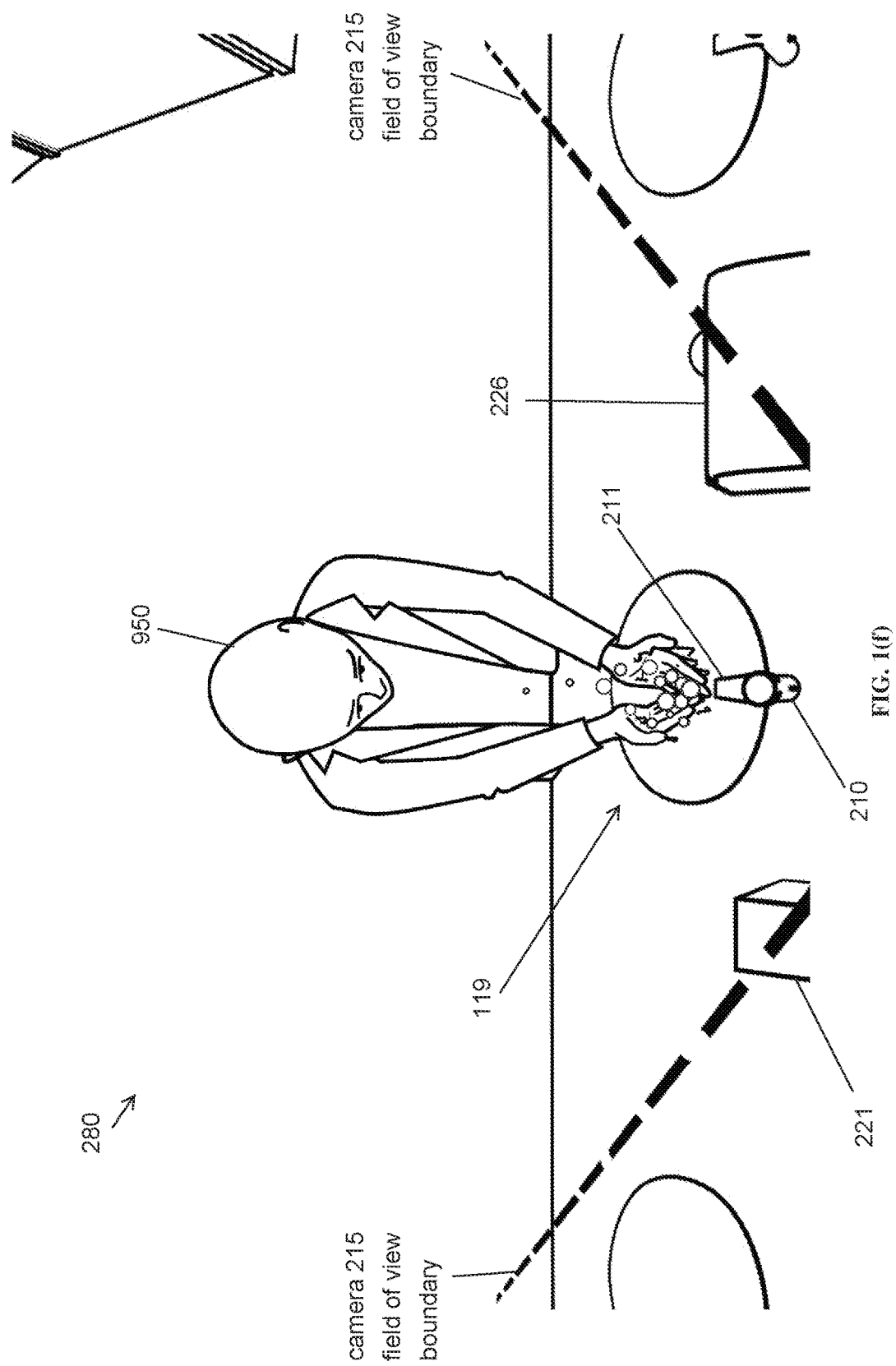

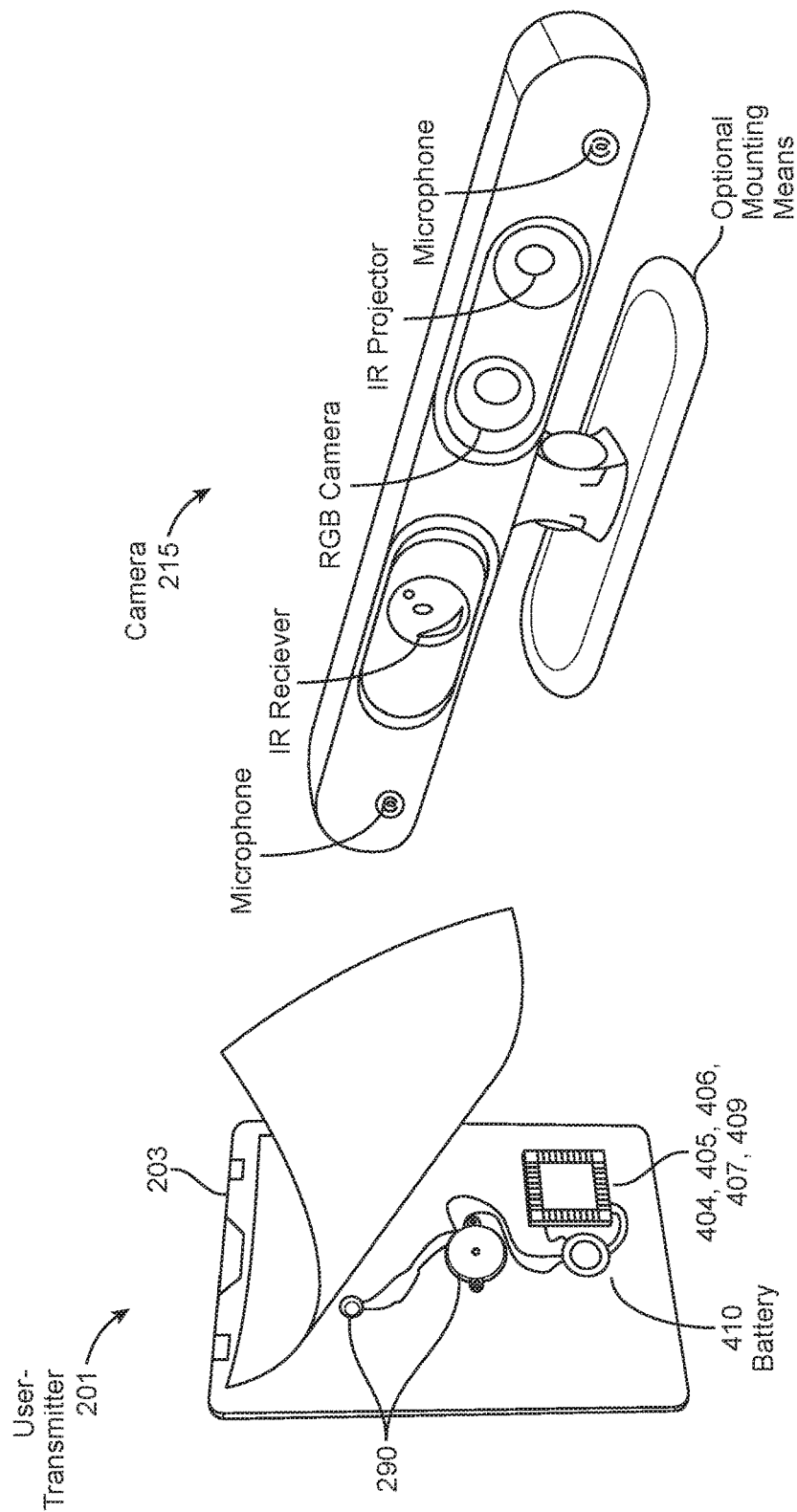

METHOD AND SYSTEM FOR HAND WASHING COMPLIANCE

PRIORITY NOTICE

The present application claims priority to PCT Application No. PCT/US16/26711 filed on Apr. 8, 2016, and which is hereby incorporated by reference in its entirety, that also claims priority to CN 2015/10173233.6 filed Apr. 13, 2015.

CROSS REFERENCE TO RELATED PATENT APPLICATIONS

The present application makes no reference to any other related filed patent applications.

STATEMENT REGARDING FEDERAL SPONSORSHIP

No part of this invention was a result of any federally sponsored research.

TECHNICAL FIELD OF THE INVENTION

The present invention relates in general to user hand washing compliance with proper hand washing techniques and more specifically to methods and/or systems for active monitoring and validation to ensure actual user compliance with proper hand washing techniques.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Obviously proper hand washing practices are critical in many industries. Such industries include food preparation (including processing and manufacturing), food cooking and serving (e.g. restaurants and catering), medical treatment services, medical device and pharmaceutical production and manufacturing, in various laboratory research and testing environments where minimizing various contaminants may be critical, and the like. Proper hand washing is the primary means by which infection is not spread and that food is preserved from contamination. Proper hand washing also plays an important role in maintaining purity of pharmaceuticals and medical devices.

Generally, it has fallen to employers in these various industries to provide proper training to their employees and independent contractors with respect to proper hand washing techniques, which may vary from industry to industry and from employer to employer. But compliance with proper hand washing training has largely been left to employee and independent contractor trust alone, such as the employee or independent contractor completing a log of hand washing activities. One reason for the art to rely primarily upon trust has been privacy concerns of the user, since many hand washing facilities are located within restrooms and/or bathrooms.

It may be desirable to move beyond a reliance on just trust alone and to not only encourage and properly train users, but also to actively monitor and/or validate hand washing to ensure actual compliance with proper hand washing techniques. Such active monitoring and/or validation of hand washing to ensure actual compliance may provide a benefit to entities (e.g. employers) who may be responsible for a user's hand washing compliance to mitigate against liability arising from non-compliance and/or to improve hygiene and health care of activities which typically follow and flow from hand washing.

There is a need in the art for methods and system which permit active monitoring and validation of hand washing to ensure compliance with required hand washing techniques, but that do so by maintaining appropriate privacy of the user.

It is to these ends that the present invention has been developed.

BRIEF SUMMARY OF THE INVENTION

To minimize the limitations in the prior art, and to minimize other limitations that will be apparent upon reading and understanding the present specification, the present invention describes a method and a system for user hand washing compliance.

For example, an exemplary embodiment of the method may comprise the steps of: receiving a request from the user to enter a hand-washing-compliance-area, wherein the request is received by an entry-sensor; the entry-sensor may cause initiation of a hand-washing-cycle log entry; releasing water from a washer for pre-rinsing hands of the user; releasing soap from a soap-dispenser for soaping the hands of the user; releasing water from the washer to rinse the soaped hands of the user; and providing a means-to-dry-hands from a hand-dryer for drying the hands of the user. The user may initiate each step with the user-transmitter based on physical proximity and/or with appropriate hand-gestures before a gesture-recognition-camera (camera). For example, the user may place the user-transmitter within a sufficient distance of the entry-sensor, such that the entry-sensor receives a first-wireless-transmission from the user-transmitter. Upon the user initiating each step, the camera may record each step. And at least one server (and/or a temporary-controller) may receive said recordings and validate each step as compliant or non-compliant.

Alternatively, in another exemplary embodiment, the camera may not make any recordings and validation of each phase of a given hand washing cycle may proceed by camera presenting captured object images (e.g. of limbs, hands, and digits) to a pattern recognition algorithm. The pattern recognition algorithm may then compare the captured object images to determine compliance or non-compliance with each phase of the given hand washing cycle.

It is an objective of the present invention to provide methods and system which may actively monitor, validate (confirm) and otherwise ensure that the user has engaged in proper hand washing techniques.

It is another objective of the present invention to provide methods and/or systems which may function without an undue intrusion of privacy.

It is another objective of the present invention to provide methods and/or systems which may function without undue intrusion into a daily work routine of the user.

It is another objective of the present invention to provide the methods and/or systems in a manner which is largely automated, relying upon wireless communication technologies, proximity sensing, and gesture recognition. Such gesture recognition capability may result of use of specialized camera technology.

It is another objective of the present invention to provide the methods and systems which may also detect if proper water temperature may have been used in the hand washing It is yet another objective of the present invention to provide at least a semi-permanent record of any given user's hand washing for periodic user reviews and other quality control auditing needs.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

A FIG. 1 series which may comprise FIG. 1(a) through FIG. 1(h) may depict exemplary phases and steps of a method for user hand washing compliance.

FIG. 1(c) may depict an exemplary embodiment of the user displaying a start-hand-washing-command that may be viewed (and sometimes recorded) by a camera and received by a temporary-controller or by at least one server.

FIG. 1(d) may depict an exemplary embodiment of a pre-rinse phase, wherein the user wets hands beneath a washer, wherein this conduct may be viewed (and sometimes recorded) by the camera and wherein this conduct data may be validated as an appropriate pre-rinse phase.

FIG. 1(f) may depict an exemplary embodiment a rinse (washing) phase, wherein the user rinses hands of soap from beneath the washer, wherein this conduct data may be viewed (and sometimes recorded) by the camera and wherein this conduct data may be validated as an appropriate rinse phase.

FIG. 4(a) may depict an exemplary embodiment of subcomponents of the user-transmitter in an identification-card embodiment.

FIG. 5 may depict an exemplary embodiment of subcomponents of a camera.

Figure 1A:
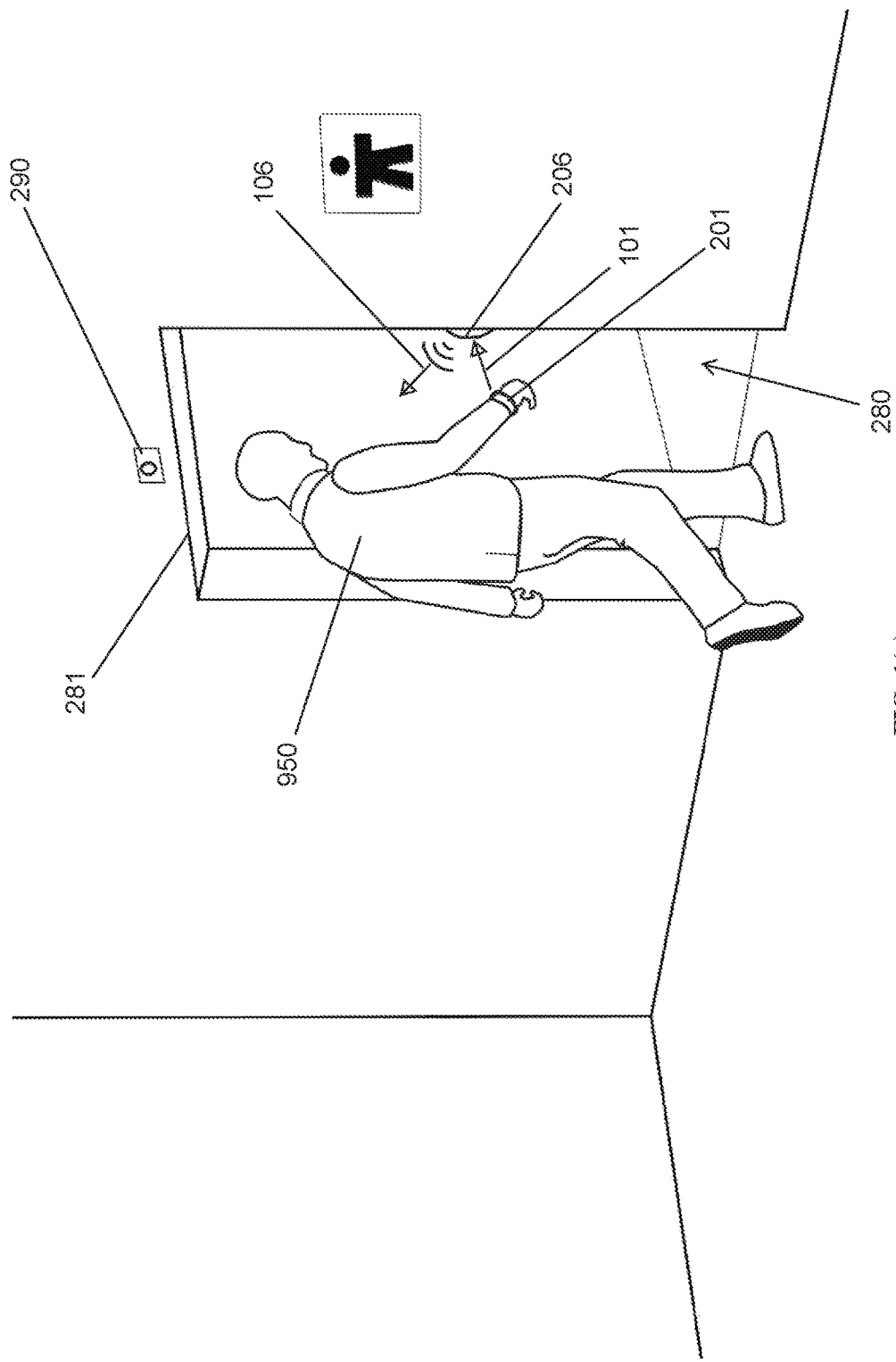
FIG. 1(a) may depict an exemplary embodiment of a user entering or about to enter a hand-washing-compliance-area, wherein a user-transmitter physically associated with the user may be in sufficient proximity for the user-transmitter to transmit a first-wireless-transmission to an entry-sensor, wherein the entry-sensor may be located at an entrance to the hand-washing-compliance-area.
Figure 1B:
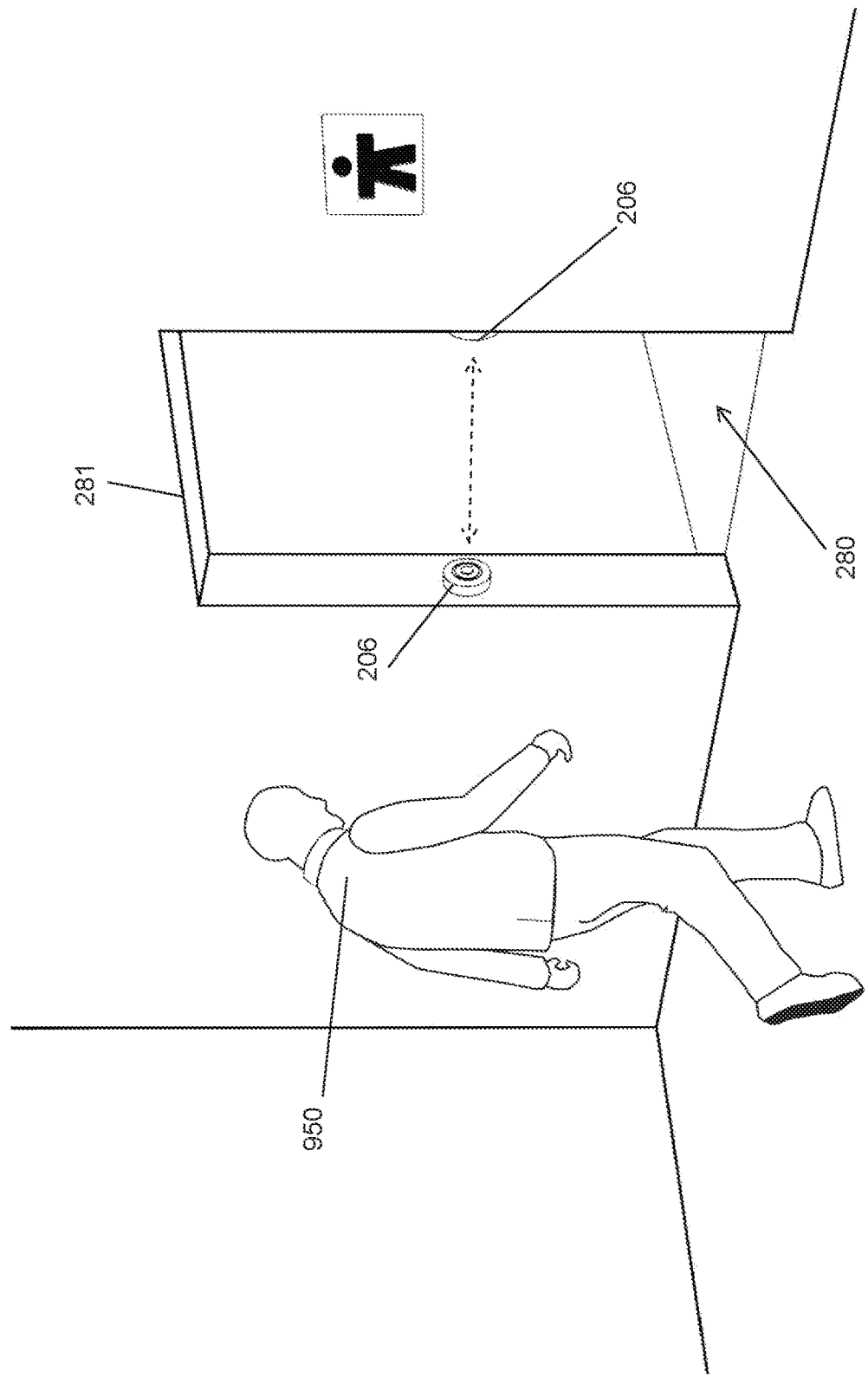
FIG. 1(b) may depict an exemplary embodiment of a user about to enter the hand-washing-compliance-area, wherein the entry-sensor here may use a threshold sensor to detect the user entering the hand-washing-compliance-area, wherein the entry-sensor may be located at an entrance to the hand-washing-compliance-area.

REFERENCE NUMERAL SCHEDULE 101 first-wireless-transmission 101
102 user-data 102
103 unique-user-ID 103
106 second-wireless-transmission 106
107 User-hand-washing-log 107
108 hand-washing-cycle 108
110 start-hand-washing-command 110
111 first-recording 111
112 second-recording 112
113 third-recording 113
114 fourth-recording 114
155 fifth-recording 155
115 hand-gestures 115
116 defined-hand-gestures 116
117 defined-pre-rinse-gestures 117
118 defined-soaping-gestures 118
119 defined-washing-gestures 119
120 defined-drying-gestures 120
121 defined-first-duration 121
122 defined-second-duration 122
123 defined-third-duration 123
124 defined-fourth-duration 124
125 defined-fifth-duration 125
126 first-error-message 126
127 second-error-message 127
128 third-error-message 128
129 fourth-error-message 129
130 fifth-error-message 130
160 sixth-error-message 160
131 first-turn-on-signal 131
132 second-turn-on-signal 132
145 third-turn-on-signal 145
135 third-wireless-transmission 135
140 fourth-wireless-transmission 140
150 fifth-wireless-transmission 150

165 hand-washing-cycle-completion-signal 165
170 completion-feedback-signal 170
175 validate-entire-cycle-command 175
176 final-overall-validation-message 176
177 operator-review-notification 177
180 feedback-signal 180
200 system 200
201 user-transmitter 201
202 wrist-band 202
203 identification-card 203
404 wireless-transmitter 404
405 wireless-receiver 405
406 user-memory 406
407 optional-function-chip 407
409 optional-processor 409
410 battery 410
206 entry-sensor 206
210 washer 210
211 means for dispensing water 211
215 camera 215
221 soap-dispenser 221
226 hand-dryer 226
231 at least one server 231
332 processor 332
333 memory 333
334 network-adapter 334
335 server-power-source 335
240 temporary-controller 240
250 wireless-router 250
260 operator-computing-device 260
270 user-computing-device 270
280 hand-washing-compliance-area 280
281 entrance 281
290 feedback-means 290
801 WAN 801
900 operator 900
950 user 950

DETAILED DESCRIPTION OF THE INVENTION

Methods and systems for user hand washing compliance are described and disclosed. Overall, these methods and systems may rely upon (1) wireless communications among the various components of the systems; and (2) upon a camera which may be configured for gesture recognition, including thermal imaging, such that gestures typical of various phases of hand washing may be monitored and/or validated for compliance. In some embodiments, this gesture recognition capability of the camera may also be used to initiate various phases of hand washing. In some embodiments, predominantly wireless communications among the various components of the system may be used to initiate various phases of hand washing, which may also involve activation of communications based on physical proximity of the user and/or of a user-transmitter with the various components. In some embodiments, both the camera and the wireless communications among the various components of the system may be used to initiate various phases of hand washing. In some embodiments, timing of a given hand washing phase may also be tracked and timing may be used to progress from one phase to another.

Washing of the hands may comprise the following main phases: (1) pre-rinsing the hands with water to wet the hands, i.e. a pre-rinse phase; (2) soaping (i.e. lathering) the hands with a soap (i.e. detergent or cleaner), i.e. a soaping phase; (3) washing and rinsing the soaped hands with water to remove the soap, i.e. a rinsing phase; and (4) drying the wet hands, i.e. a drying phase. Depending upon constraints and objectives, additional phases and steps within a given phase may be added or removed. For example, if conserving water may be deemed important, then the pre-rinse phase may be removed or shortened. For example, if washing hands may be for medical purposes, then antibacterial soaps may be used; and/or it may be desirable to keep fingertips up above the rest of the hand and forearm so as to encourage any contamination to run away from the fingers; and/or to use equipment that does not require touching the hands and fingers to any controls for turning water on or off and/or for dispensing the soap.

It may be desirable to encourage, properly train, monitor, ensure, and/or validate such hand washing phases being performed by a user, such that an entity who may be responsible for the user's hand washing compliance may mitigate liability arising from non-compliance and/or to improve hygiene and health care of activities which typically follow hand washing. Obviously proper hand washing may be critical on food preparation, food services, medical treatment, and medical and life science research industries.

An exemplary embodiment of the method may comprise the steps of: receiving a request from the user to enter a hand-washing-compliance-area, wherein the request is received by an entry-sensor; the entry-sensor may cause initiation of a hand-washing-cycle log entry; releasing water from a washer for pre-rinsing hands of the user; releasing soap from a soap-dispenser for soaping the hands of the user; releasing water from the washer to rinse the soaped hands of the user; and providing a means-to-dry-hands from a hand-dryer for drying the hands of the user. The user may initiate each step with the user-transmitter based on physical proximity and/or with appropriate hand-gestures before a gesture-recognition-camera (camera). For example, the user may place the user-transmitter within a sufficient distance of the entry-sensor, such that the entry-sensor receives a first-wireless-transmission from the user-transmitter. Upon the user initiating each step, the gesture-recognition-camera records each step. And at least one server (and/or a temporary-controller) may receive said recordings and validate each step as compliant or non-compliant.

In some embodiments, the user initiating each step may occur by the user making appropriate hand-gestures at appropriate locations. Such initiation may by be facilitated by the camera both recognizing an appropriate hand-gesture (e.g. a defined-pre-rinse-gestures, a defined-soaping-gestures, a defined-washing-gestures, a defined-hand-gestures, and/or a defined-drying-gestures) and by the camera recognizing that the appropriate hand-gesture may be occurring in an appropriate three dimensional location. The gesture-recognition-camera may be configured to recognize stereoscopic events.

For example, and without limiting the scope of the present invention, the user making defined-washing-gestures below a faucet of the washer, may be recorded by the camera as both an appropriate hand-gesture and as occurring in a proper three dimensional location, such that the camera causes a signal to be sent to the washer to turn on the running of water. Likewise, when the user removes hands from this appropriate three dimensional location, the camera may recognize this and cause another signal to be sent to the washer such that the water is turned off.

For example, and without limiting the scope of the present invention, the user making defined-soaping-gestures below the soap-dispenser, may be recorded by the camera as both an appropriate hand-gesture and as occurring in a recognized three dimensional location, such that camera causes a signal to be sent to the soap-dispenser to dispense soap. Depending upon the embodiment, soap may be dispensed continuously for a defined time period or one or more metered bursts of soap dispensing may be used. Likewise, when the user removes hands from this appropriate three dimensional location, the camera may recognize this and cause another signal to be sent to the soap-dispenser such that soap may no longer be dispensed.

For example, and without limiting the scope of the present invention, the user making defined-drying-gestures within a proximity of hand-dryer, may be recorded by the camera as both an appropriate hand-gesture and as occurring in a recognized three dimensional location, such that camera causes a signal to be sent to the hand-dryer to either blow air or to provide a towel. Likewise, when the user removes hands from this appropriate three dimensional location, the camera may recognize this and cause another signal to be sent to the hand-dryer such that air blowing ceases or no more towels may be provided.

In other embodiments, in the above three examples, the signals to start and stop the washer, the soap-dispenser, and the hand-dryer may emanate from the at least one server and/or the temporary-controller after the at least one server and/or the temporary-controller validates the appropriate recording received from the camera. In other exemplary embodiments, no image recordings may be taken by the camera, and instead validation may occur in near real-time by comparing observed (viewed) images with a pattern recognition algorithm. Note, "near" here may denote that it may take some processing time to compute validation of viewed gestures.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

FIG. 1 series may comprise FIG. 1(a) through FIG. 1(g), wherein each such FIG. may depict exemplary phases of a method 100 for user hand washing compliance. In exemplary embodiments, method 100 may comprise seven main phases: (1) an entry phase; (2) a start hand-washing-cycle phase; (3) a pre-rinse phase; (4) a soaping (i.e. lathering) phase; (5) a rinse phase; (6) a drying phase; and (7) a completion phase. Each phase may comprise a plurality of various steps. Not all embodiments may include each of these seven phases. For example, and without limiting the scope of the present invention, the pre-rinse phase may be omitted (or shortened) where conservation of water may be deemed material. For example, and without limiting the scope of the present invention, the drying phase may be omitted where such a phase may not be part of a hand washing compliance policy or procedure or for budget concerns.

FIG. 1(a) may depict an exemplary embodiment of a user 950 entering or about to enter a hand-washing-compliance-area 280. A user-transmitter 201 may be physically associated with user 950 (e.g. on a lanyard around user's 950 neck, on a wrist of user 950, or within a pocket of user 950). When user-transmitter 201 may be in sufficient proximity to an entry-sensor 206, then user-transmitter 201 may transmit a first-wireless-transmission 101 to entry-sensor 206. Entry-sensor 206 may be located at an entrance 281 to hand-washing-compliance-area 280. Entrance 281 may be an access-point for user 950 to gain entry to hand-washing-compliance-area 280.

In some embodiments, first-wireless-transmission 101 may be a request from user 950 to enter hand-washing-compliance-area 280. In some embodiments, first-wireless-transmission 101 may comprise transmitting a unique-user-ID 103 associated with that particular user 950. In some embodiments, user-transmitter 201 may non-transitorily store user-data 102. User-data 102 may be wirelessly transmitted in first-wireless-transmission 101. In some embodiments, user-data 102 may be wirelessly transmitted from any wireless transmission, not just first-wireless-transmission 101, emanating from user-transmitter 201. In some embodiments, the user-data 102 may comprise unique-user-ID 103. Unique-user-ID 103 may be associated with a particular user 950. In some embodiments, the user-data 102 may comprise a name of the user and/or a job title of the user.

Figure 2:
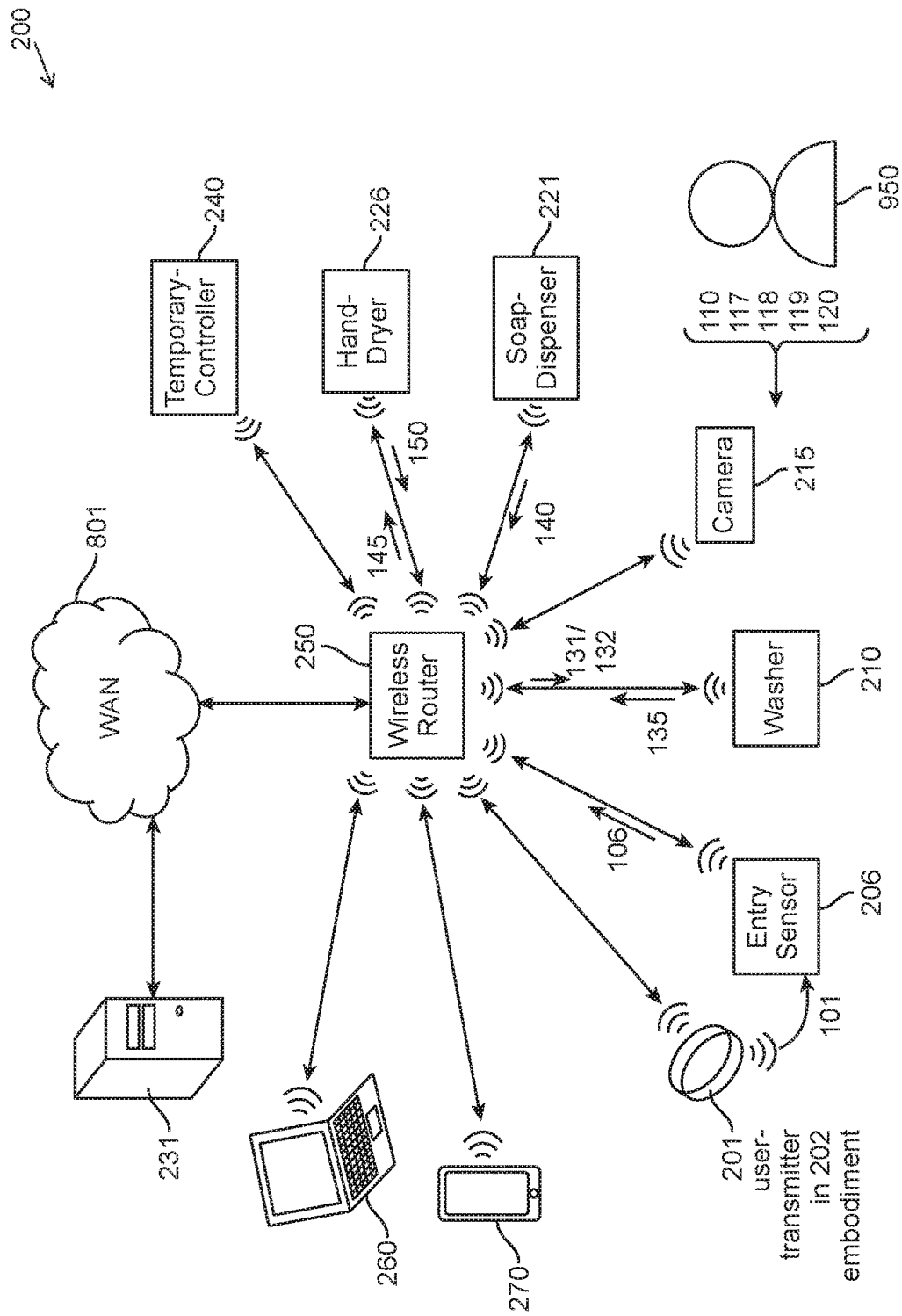
FIG. 2 may depict an exemplary embodiment of a system for user hand washing compliance, wherein some components of such a system may be depicted, with some potential communication relationships of these system components.
Figure 2A:
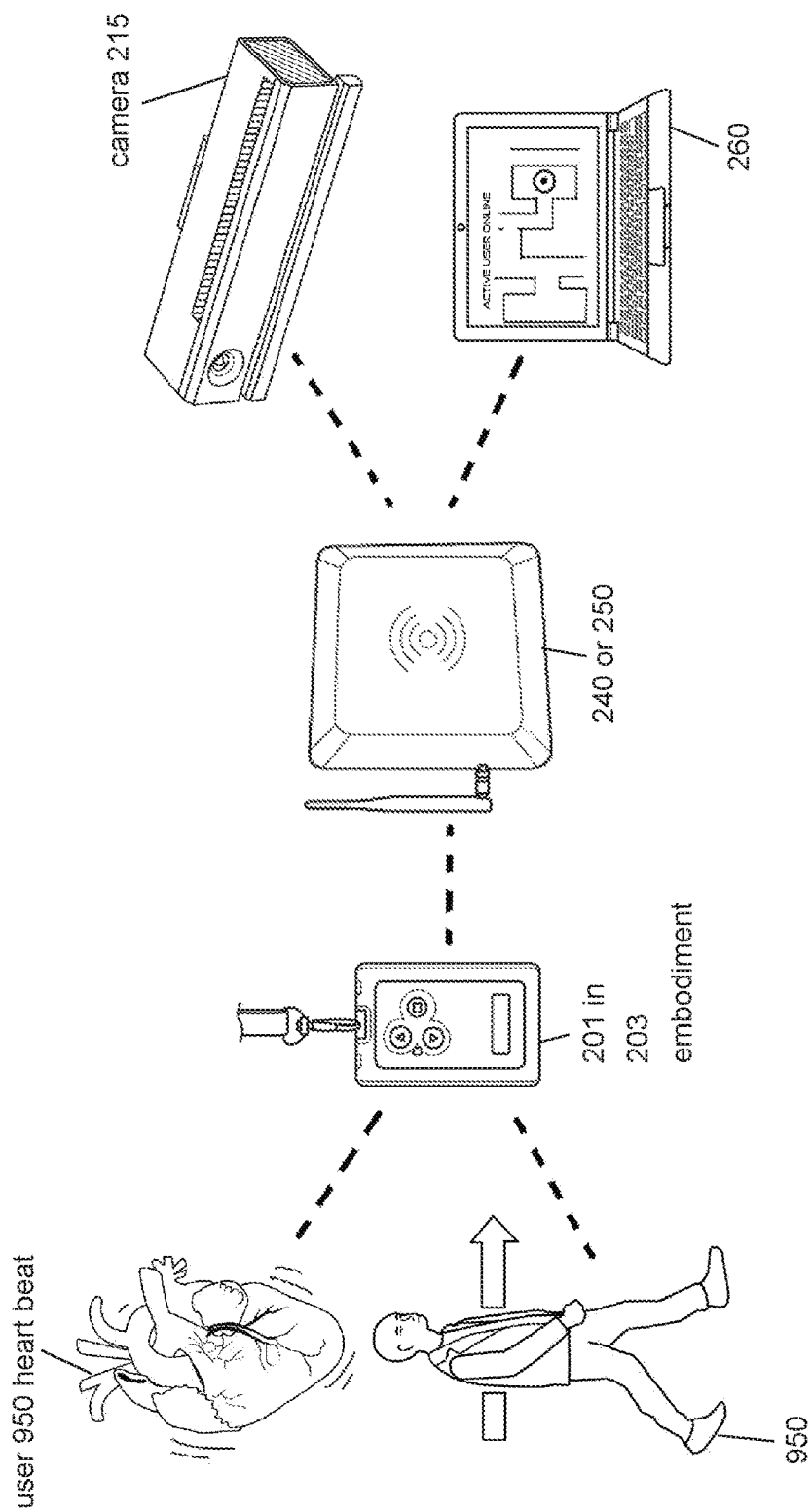
FIG. 2(a) may depict an exemplary embodiment of how the user-transmitter may be used to determine the user's location within a work site environment.

In some embodiments, user-transmitter 201 may be housed within and/or may be in integral physical contact with a wrist band 202 (see e.g, FIG. 1(a) and FIG. 2), an identification card (badge) 203 (see e.g., FIG. 2(a) and FIG. 4(a)), a keychain, and/or a similar device. For example, and without limiting the scope of the present invention, user-transmitter 201 may be a device which transmits at least one type of wireless signal. Such a user-transmitter 201 may be housed within bracelet (i.e. wrist band) 202 or within identification card 203. Such an identification card 203 may be worn around the user's neck on a lanyard or kept within a pocket of user 950. Identification card 203 may visually display a photograph, name, and job title of user 950, as well as other information deemed important by an entity or employer. For example, and without limiting the scope of the present invention, user-transmitter 201 may function as a punch card for a time clock, i.e. user-transmitter 201 may be used to track employee time, such as when the employee may be working, may be on break and/or lunch, and the like.

In some embodiments, user-transmitter 201 may comprise a wireless-transmitter 404. In some embodiments, wireless-transmitter 404 may be configured for wireless transmission using a wireless communication protocol selected from one or more of the group comprising: Bluetooth®, WiFi, radio frequency ID (RFID), near field communication (NFC), and the like.

In some embodiments, user-transmitter 201 (e.g. comprising wireless-transmitter 404) may be configured for wireless transmission using either an active wireless communication protocol or a passive wireless communication protocol. In exemplary embodiments, user-transmitter 201 may be configured to transmit wireless signals via a passive wireless technology such as RFID or NFC. In such embodiments, user-transmitter 201 may derive power to transmit from another device (e.g. from entry-sensor 206) that may in sufficient proximity to user-transmitter 201. Sufficient proximity may vary according to passive wireless communication technology employed (NFC or RFID) and where user 950 may be storing user-transmitter 201 (e.g. within a pocket, around a wrist, or on a lanyard). For example, and without limiting the scope of the present invention, in some embodiments the sufficient proximity between user-transmitter 201 and entry-sensor 206 may be within 10 centimeters (cm). See e.g, FIG. 1(a), where the distance in FIG. 1(a) may be within 10 centimeters (cm).

In some exemplary embodiments, where user-transmitter 201 may be configured for active wireless communication, user-transmitter 201 may be tracked via wireless triangulation, using a plurality of wireless receiving sensors located at various positions around the work site environment, including a plurality of such sensors that may be located within hand-washing-compliance-area 280. Such a plurality of sensors may enable tracking of user-transmitter 201 from room to room within the work site environment and within hand-washing-compliance-area 280 and in near real-time. Note, "near" here may denote that it may take some processing time to commute locations via triangulation. Such receiving wireless sensors may wireless report (communicate) directly to wireless-router 250 and/or indirectly to at least one server 231 and/or to temporary-controller 240. Temporary-controller 240 and/or at least one server 231 may then communicate such dynamic location information of user-transmitter 201 to operator computing-device 260. Then such dynamic location may be visually displayed over a map of the work site environment on an operator-graphical-user-interface (operator-GUI). Additionally, in some embodiments, user-transmitter 201 may comprise optional-function-chip 407, which may comprise a heartbeat sensor, accelerometer, and/or a vibration detector, which additional functions may add redundancy to help in determining if user 950 may be wearing user-transmitter 201 as may be required. See e.g., FIG. 2(*a*) (note the tracking sensors may be not be depicted in FIG. 2(*a*)).

In active embodiments, user-transmitter 201 may have its own power source, such as a battery 410 (see e.g., FIG. 4), which may be rechargeable.

In some embodiments, user-transmitter 201 may comprise a wireless-receiver 405. In some embodiments, wireless-receiver 405 may be configured for receiving wireless transmissions using one or more wireless communication protocols selected from the group comprising: Bluetooth®, WiFi, RFID, NFC, and the like. In some embodiments, wireless-receiver 405 may be configured for receiving wireless transmissions from one or more of at least one server 231, a temporary-controller 240, entry-sensor 206, a washer 210, a camera 215, a soap-dispenser 221, a hand-dryer 226, a wireless-router 250, an operator-computing-device 260, a user-computing-device 270, and the like. In some embodiments, wireless-transmitter 404 and wireless-receiver 405 may share the same hardware as an antenna configured for various wireless communications, see e.g., FIG. 4.

In some embodiments, user-transmitter 201 may comprise a heartbeat sensor 407. Such heartbeat detection may permit method 100 and/or system 200 to determine if user 950 may be wearing user-transmitter 201. In some embodiments, heartbeat sensor 407 may also comprise vibration detection and/or motion detection via an accelerometer chip. Such vibration detection (motion detection) may aid in tracking user 950 motion and movement. See e.g., FIG. 2(*a*). The heartbeat sensor 407 and/or the vibration detector 407 may aid method 100 and/or system 200 in determining if user 950 may be currently wearing user-transmitter 201. Such information may be used to determine if that particular user 950 may have been trying to cheat (whether intentionally or unintentionally) method 100 and/or system 200 by not wearing user-transmitter 201 when required to do so (e.g. when in hand-washing-compliance-area 280).

In some embodiments, user-transmitter 201 may comprise a means for providing feedback-signal 180 and/or completion-feedback-signal 170. In some embodiments, the means for providing feedback-signal 180 and/or completion-feedback-signal 170 may comprise feedback-means 290. Feedback means 290 may comprise an audible signal generator (e.g. a buzzer and/or beeper, speaker, etc.) and/or a visual signal generator (e.g. at least one LED or LEDs of different colors). For example, and without limiting the scope of the present invention, user-transmitter 201 may display a lit red LED, which may flash or remain constantly on, when user 950 does not properly conduct hand washing. Such a red LED may indicate to others that this particular user 950 did no properly conduct hand washing. In some embodiments, feedback-means 290, for providing feedback-signal 180 and/or completion-feedback-signal 170 may comprise a vibrator, such that user 950 may feel the vibrations. Such vibrations may operate a reminder to user 950 to adhere to proper hand washing practices when in hand-washing-compliance-area 280.

In some embodiments, wireless-transmitter 201 may also be configured for wired communications with an operator-computing-device and/or with a user-computing device. Such wire communication may be via USB (universal serial bus) connections and cables, mini-USB connections and cables, and similar charging and/or data communication cables. Such wired communication may facilitate programming and/or updating user-memory 406 with user-data 102, such as unique-user-ID 103. Such wired communication may facilitate charging of batteries of user-transmitter 201 in embodiments where user-transmitter 201 may have its own power source.

In some embodiments, entry-sensor 206 may comprise a sensor-receiver, a sensor-transmitter, a sensor-power-source, and a feedback-means 290 for providing feedback-signal 180 and/or completion-feedback-signal 170. The sensor-receiver may be configured to receive first-wireless-transmission 101. In some embodiments, the sensor-receiver may be configured to receive wireless transmission from at least one server 231, temporary-controller 240, and/or operator-computing-device 260. The sensor-transmitter may be configured to wirelessly transmit a second-wireless-transmission 106. The sensor-power-source may be configured to provide electrical power to the sensor-receiver and to the sensor-transmitter.

In some embodiments, the feedback-means 290 for providing feedback-signal 180 and/or completion-feedback-signal 170 may comprise an audible signal generator (e.g. a buzzer and/or beeper, speaker, etc.) and/or a visual signal generator (e.g. at least one LED or LEDs of different colors). This feedback-means 290 for providing feedback-signal 180 and/or completion-feedback-signal 170 may also be a component of other components of system 200 that method 100 may use as disclosed herein.

In some embodiments (e.g. passive user-transmitter 201), entry-sensor 206 (e.g. via the sensor-power-source and the sensor-transmitter) may be configured to wirelessly provide power to user-transmitter 201, when the user-transmitter 201 may be within sufficient proximity from entry-sensor 206. (e.g. within 10 cm in some embodiments).

In some embodiments, the sensor-transmitter may be configured for wireless transmission using a wireless communication protocol selected from one or more of the group comprising: Bluetooth®, WiFi, RFID, NFC, and the like. In some embodiments, the sensor-receiver may be configured for receiving wireless transmissions using a wireless communication protocol selected from one or more of the group comprising: Bluetooth®, WiFi, RFID, NFC, and the like.

In some embodiments, entry-sensor 206 may be configured to control access to hand-washing-compliance-area 280 by unlocking an entry door permitting access to hand-washing-compliance-area 280. In such embodiments, entry-sensor 206 may be in communication (e.g. wired or wireless) with an electronic locking means. In such embodiments, when user-transmitter 201 may be brought sufficiently close to entry-sensor 206, then entry-sensor 206 upon receiving first-wireless-transmission 101 from user-transmitter 201, entry-sensor 206 may then send a signal to the electronic locking means unlocking the door to hand-washing-compliance-area 280 so that user 950 may then enter.

In some embodiments, entry-sensor 206 may comprise a threshold sensor. See e.g., FIG. 1(b). The threshold sensor may be a motion sensor and/or a sensor configured to detect a break in an emitted and reflected beam. Such a threshold sensor may be mounted in a doorway (entryway) to hand-washing-compliance-area 280. In some embodiments, such a threshold sensor may be used in place of detecting and receiving first-wireless-transmission 101 from user-transmitter 201. Or in some embodiments, such a threshold sensor may be used in conjunction with detecting and receiving first-wireless-transmission 101 from user-transmitter 201, i.e. as a source of redundancy and verification of detecting and receiving first-wireless-transmission 101 from user-transmitter 201.

In some embodiments, entry-sensor 206 receipt of first-wireless-transmission 101 from user-transmitter 201 may initiate transmission of second-wireless-transmission 106. See e.g., FIG. 1(a). Second-wireless-transmission 106 may comprise information logging initiation of a hand-washing-cycle 108 in a user-hand-washing-log 107. Hand-washing-cycle 108 may comprise at least one log entry pertaining to a given user's 950 interactions with method 100 and/or system 200. User-hand-washing-log 107 may be a database maintained on memory 333 in communication with the at least one server 231. Each hand-washing-cycle 108 may comprise a plurality of log entries pertaining to a given user's 950 interactions with method 100 and/or system 200. User-hand-washing-log 107 may comprise a plurality of hand-washing-cycle 108 entries.

In some embodiments, second-wireless-transmission 106 may be directed to at least one server 231, or temporarily to temporary-controller 240. Note, this wireless communication is not depicted in FIG. 1(a) as at least one server 231 and temporarily to temporary-controller 240 are not depicted in FIG. 1(a); however, this communication relationship is shown in FIG. 2. In some embodiments, second-wireless-transmission 106 may comprise information logging initiation of hand-washing-cycle 108. This information of second-wireless-transmission 106 may comprise: (1) information contained within first-wireless-transmission 101 (e.g. unique-user-ID 103, user's name, and/or user's job title); (2) a date of receiving first-wireless-transmission 101; and (3) a time of receiving first-wireless-transmission 101. The information contained within second-wireless-transmission 106 may constitute a first log entry in any given hand-washing-cycle 108.

In some embodiments, hand-washing-compliance-area 280 may be an area wherein the physical area may bound a three dimensional space. This three dimensional space may comprise entry-sensor 206, washer 210, camera 215, soap-dispenser 221, and in some embodiments, hand-dryer 226. In some embodiments, wireless router 250 may also be located within this three dimensional space. In some embodiments, temporary-controller 240 may also be located within this three dimensional space. In some embodiments, hand-washing-compliance-area 280 may be a restroom, a bathroom, a washroom, and the like. See e.g., the FIG. 1 series of figures.

FIG. 1(c) may depict an exemplary embodiment of user 950 displaying a start-hand-washing-command 110 that may be recorded by camera 215 (or optionally recorded by camera 215) and received by temporary-controller 240 or by at least one server 231.

In some embodiments, temporary-controller 240 and/or at least one server 231 receipt of second-wireless-transmission 106 may trigger several results. In some embodiments, these results may include temporary-controller 240 and/or at least one server 231 sending signals to be received by camera 215, washer 210, soap-dispenser, and/or hand-dryer 226, such that these components may then power up and/or enter a status ready for interaction with user 950. In some embodiments, these results may include initiation of the pre-rinse phase, followed by the soaping phase, followed by the rinse phase, followed by the drying phase, and then followed by the completion phase, wherein each phase, including transition to the next phase may be controlled by various timers applicable to each phase and each transition.

In some embodiments, user 950 may initiate a start to any particular phase by user 950 conduct (e.g. gesturing) as recorded by camera 215. In some embodiments, start-hand-washing-command 110 may be user 950 conduct observed (or optionally recorded) by camera 215. See e.g., FIG. 1(c), where user 950 may be displaying start-hand-washing-command 110 as observed by camera 215. In this example, start-hand-washing-command 110 may be user 950 holding both hands up with palms facing and visible to camera 215. Of course, in other embodiments, other start-hand-washing-command 110 may be utilized.

In some embodiments, camera 215 may be a gesture-recognition-camera. In some embodiments, camera 215 may be configured to recognize stereoscopic events (i.e. a three dimensional location of an event before camera 215). In some embodiments, camera 215 may be configured to view and/or record thermal images, i.e. camera 215 may also be an IR (infrared) camera. In some embodiments, camera 215 may be a gesture-recognition-camera, a thermal imaging camera, and configured to detect stereoscopic events within camera's 215 field of view.

In some embodiments, camera 215 may be a stereoscopic camera capable of seeing (observing and/or viewing) in 3D (three dimensions). See e.g., FIG. 5 regarding general camera 215 features. That is, camera 215 may be able to calculate depth and volume of various objects within camera 215 field of view. Camera 215 may comprise a light projector (emitter) and light receiving sensor (receiver). In some embodiments, the light may be laser light. In further embodiments, the laser light may be infrared (IR) laser light. In such embodiments, the light projector may be projecting IR laser light into a field of view of camera 215. Such projected laser light may reflect off of various objects within the field of view and may then be received by the light receiver (sensor). The light receiver may comprise a monochrome CMOS (complimentary metal-oxide semiconductor) sensor for detecting the reflected IR laser light. By analyzing the received reflected IR laser light and a time of flight for how long it may take the reflected IR laser light to be received by the light receiver (sensor), the software may generate an accurate and precise 3D map of the field of view. Such time of flight 3D depth tracking and mapping technology may be tuned for operation at distances of 1.5 meters or less from the objects being measured to camera 215. Continual projections of such IR laser light and continual receipt of reflected IR laser light may enable camera 215 to see depth and near real-time changes (i.e. movement) in the field of view. Additionally, use of IR light may allow such 3D mapping and motion tracking to operate with or without a presence of visible light.

In some embodiments, camera 215 may comprise digital-optics (i.e. lenses) which may recognize facial features, appendage (limb) anatomy, and hand and finger (digit) anatomy. For example, and without limiting the scope of the present invention, camera's 215 digital-optics may recognize numerous shapes and/or length (size) of shapes. For example, camera's 215 digital-optics may recognize how many limbs and/or hands and/or digits may be within the field of view. For example, camera's 215 digital-optics may be able to determine a length of an arm within the field of view. In some embodiments, the digital-optics may comprise digital lenses, such as RBG (red blue green) video capability, as well as the light projector and light receiver (sensor). Camera's 215 digital-optics may recognize if user 950 may be missing fingers, thumbs, hands, or limbs. Camera's 215 digital-optics may recognize thumbs from fingers and fingers from thumbs, and where each finger and thumb should be in relation to each hand.

With respect to user 950 hands, Camera's 215 digital-optics may recognize not only the number of hands (one, two, or none), but may also be able to differentiate a palm side (palmar) of the hands from an opposing dorsal side of the hands.

With respect to user 950 hands, camera's 215 digital-optics may recognize if the palms of two hands are touching and rubbing against each other. Camera's 215 digital-optics may recognize where the hands may be located in 3D space. Camera's 215 digital-optics may be able to differentiate between palms in physical contact and rubbing; from two dorsal sides of the hands in physical contact and rubbing.

In an exemplary embodiment, camera 215 is not comparing digital 2D (two dimensional) images of hands for an output decision. Rather, method 100 and/or system 200 may be watching for, in 3D, whether palms may be coming together, to make a decision on proper or improper hand washing. Method 100, via the software, may be comparing viewed shapes and 3D positions of such viewed shapes against a 3D model of an ideal set of shapes and positions of the pattern recognition algorithm.

In exemplary embodiments, camera 215 may also comprise an infrared (IR) camera or other equivalent thermal sensor. In such embodiments, observing heat emissions from running water and/or from the surface of hands may aid in determining if proper hand washing has occurred or may be occurring. With IR camera (infrared) functionality proper water temperature use may be verified.

In some embodiments, observed temperature ranges may be assigned different colors for display purposes. For example, and without limiting the scope of the present invention, hot may be assigned to red, warm assigned may be assigned to yellow, and cold may be assigned to blue. With IR camera functionality, verifying actual use of water during pre-rinse and/or during washing may be made easier and more reliable because hot water (but not dangerously hot) over warm hands may provide a useful color contrast; and/or cold water over warm hands may also provide a useful color contrast as picked up by the IR camera.

Including IR camera functionality makes it much more difficult for user 950 to cheat method 100 and/or system 200. For example, with IR camera functionality, method 100 and/or system 200 may be able to differentiate between artificial hands and living humans hands, because living human hands will often have a different surface temperature profile than that of artificial hands.

With respect to user 950 facial recognition, camera's 215 digital-optics may recognize and separate employees from nonemployees to enable user 950 identification. Camera's 215 digital-optics may recognize and separate those users 950 who must adhere to proper hand washing from those who do not. In some embodiments, such recognition and differentiation, via camera 215, may be by facial feature recognition. Specific user 950 anatomical features, such as limb, hand, and digit morphology (e.g. number and size) may also be used to augment recognition and/or identification of various users 950. Such user 950 identification by facial feature recognition and/or by limb, hand and digit morphology may make use of identification via user-transmitter 201 obsolete or redundant. In some embodiments, redundancies may be exemplary to provide backup and as a means to confirm primary identification methods, such as facial feature recognition.

In some embodiments, the light projector and light receiver may also be used to aid in user 950 identification. In such embodiments, special and/or unique patterns may be seen by reflected received IR laser light. Such special and/or unique patterns may be located on exterior surfaces of user-transmitter 201, uniforms, clothing, clothing accessories (e.g. belts), and/or user 950 skin, i.e. in the form of a tattoo. Such special and/or unique patterns may be predominantly visible under IR light. Such special and/or unique patterns may be unique to each specific user 950. Use of such special and/or unique patterns may be in addition to using facial feature recognition; limb, hand, and digit morphology observation; and/or identification of user 950 via user-transmitter 201.

In some embodiments, camera 215 may also comprise one or more microphones. Such microphones may also be located in washer 210, soap-dispenser 221, and/or hand-dryer 226. Such microphone may be configured to sense various sounds emanating within hand-washing-compliance-area 280, such as a sound of running water, a sound of soap being dispensed, and a sound of hands being dried. Use of such microphones may increase the reliability of method 100 and/or system 200. In some embodiments, the one or more microphones may be arranged in an array of three or more microphones. Such an array of microphones may aid in differentiating human sounds from non-human sounds and in a direction of sounds.

In some embodiments, camera 215 may comprise digital-optics (as discussed above), a camera-receiver, a camera-transmitter, a camera-power-source, a camera-memory, a camera-processor, and a feedback-means 290 for providing feedback-signal 180 and/or completion-feedback-signal 170.

In some embodiments, the digital-optics may comprise at least one adjustable lens, at least one light projector, at least one light receiver (sensor), and the like. In some embodiments, at least one adjustable lens may be configured for capturing images of objects within camera's 215 field of view in red, green, and blue colors. In some embodiments, the digital-optics of camera 215 may also comprise thermal-imaging-optics, i.e. the IR camera. In some embodiments, the digital-optics may comprise camera-software (i.e. camera-firmware). The camera-software may instruct the camera-processor how to process images received (i.e. observed and/or viewed) by the at least one adjustable lens. The camera-software may be non-transitorily stored within the camera-memory. Together, the camera-software, the camera-processor, the at least one adjustable lens, and the camera-memory may permit camera 215 to capture (view, observe), record, and recognize: (1) facial features; (2) limb, hand, and digit morphology; (3) user 950 gestures, including hand-gestures; (4) stereoscopic events (motion) within three-dimensional (3D) space of camera's 215 field of view; (5) thermal images, e.g. of warm or cold water; and the like.

In some embodiments, the camera-receiver may be configured to receive transmissions from at least one server 231, temporary-controller 240, user-transmitter 201, entry-sensor 206, washer 210, soap-dispenser 221, hand-dryer 226, operator-computing-device 260, user-computing device 270, and the like.

In some embodiments, the camera-transmitter may be configured to wirelessly transmit a first-recording 111, a second-recording 112, a third-recording 113, a fourth-recording 114, and other recordings. First-recording 111, second-recording 112, third-recording 113 and any other recording from camera 215 may be transmitted to temporary-controller 240 and/or to at least one server 231.

In some embodiments, the camera-power-source may be configured to provide electrical power to: the digital-optics, the camera-receiver, the camera-transmitter, the camera-memory, the camera-processor, the means for providing feedback-signal 180 and/or completion-feedback-signal 170.

In some embodiments, user 950 initiating each phase and/or step may occur by user 950 making appropriate hand-gestures at appropriate locations (e.g. within hand-washing-compliance-area 280). Camera 215 may facilitate hand-gesture recognition by recognizing various defined and appropriate hand-gestures 115 (e.g. defined-hand-gestures 116, defined-pre-rinse-gestures 117, defined-soaping-gestures 118, defined-washing-gestures 119, and/or defined-drying-gestures 120). Camera 215 may also recognize whether the appropriate hand-gesture may be occurring in an appropriate three dimensional location.

For example, and without limiting the scope of the present invention, user 950 making defined-washing-gestures 119 below a faucet of washer 210, may be recorded by camera 215 as both an appropriate hand-gesture and as occurring in an appropriate three dimensional location, such that camera 215 may cause a signal received by washer 210 for washer 210 to turn on the running of water. Likewise, when user 950 may remove hands from this appropriate three dimensional location, camera 215 may recognize this and cause another signal received by washer 210 for washer 210 to turn the water off.

For example, and without limiting the scope of the present invention, user 950 making defined-soaping-gestures 118 below soap-dispenser 221, may be recorded by camera 215 as both an appropriate hand-gesture and as occurring in a recognized three dimensional location, such that camera 215 may cause a signal received by soap-dispenser 221 to dispense soap from soap-dispenser 221. Likewise, when user 950 may remove hands from this appropriate three dimensional location, camera 215 may recognize this and cause another signal to be sent to soap-dispenser 221 such that soap may no longer be dispensed.

For example, and without limiting the scope of the present invention, user 950 making defined-drying-gestures 120 within a proximity of hand-dryer 226, may be recorded by camera 215 as both an appropriate hand-gesture and as occurring in a recognized three dimensional location, such that user 950 may cause a signal to be sent to hand-dryer 226 to either blow air or to provide a towel. Likewise, when user 950 may remove hands from this appropriate three dimensional location, camera 215 may recognize this and cause another signal to be sent to hand-dryer 226 such that air blowing ceases or no more towels may be provided.

In some embodiments, user 950 may initiate a start to any particular phase by user 950 bringing user-transmitter 201 within sufficient proximity to entry-sensor 206, washer 210, soap-dispenser 221, and/or hand-dryer 226. In some embodiments, user 950 may initiate a start to any particular phase by user 950 by a combination of bringing user-transmitter 201 within sufficient proximity to a particular component and/or by performing appropriate hand-gestures 115 at appropriate locations.

In some embodiments, privacy concerns of a given user 950 may be mitigated by appropriate placement (e.g. mounting) of camera 215 within a given hand-washing-compliance-area 280, such that camera's 215 field of view may be appropriately restricted. Additionally, in some embodiments, privacy concerns of a given user 950 may be mitigated by camera 215 being configured such that the field of view may be restricted to washer 210, soap-dispenser 221, and/or hand-dryer 226. Additionally, in some embodiments, privacy concerns of a given user 950 may be mitigated by recordings of camera 215 being restricted to recognized gestures, recognized gestures within an appropriate three dimensional space, and/or thermal images.

Additionally, in some exemplary embodiments, privacy concerns of a given user 950 may be mitigated by camera 215 not making any recordings. In such embodiments, camera 215 may only be capturing (viewing and/or observing) hand and digit shapes and position in 3D information for use against an ideal set of shapes and positions of the pattern recognition algorithm. That is, in such embodiments, camera 215 may not be capturing images of hands that may be readily deciphered by a human reviewing and/or observing an output from camera 215. In such embodiments, camera 215 may be essentially acting as a sensor that may detect shapes and positioning of hands and digits of user 950. Technically, in such embodiments, camera 215 may not even be detecting hands and digits; but rather, camera 215 may be detecting objects within its 3D field of view, i.e. shapes and positions of objects may be detected by camera 215. Such detected shapes and positions of objects, in near real-time, may then be run through the pattern recognition algorithm. The pattern recognition algorithm may ask if those observed shapes and positions of observed objects sufficiently matches the ideal set of shapes and positions. The ideal set of shapes and positions may correspond to ideal hand washing of an imaginary user 950 conducting ideal hand washing through the various hand washing phases. After comparison, the pattern recognition algorithm may cause logging of compliant log entry or a non-compliant log entry. The pattern recognition algorithm may be a subcomponent of the software and may be non-transitorily stored within memory 333 of at least one server 231, or corresponding controller-memory of temporary-controller 240.

In some embodiments, receipt of second-wireless-transmission 106 by temporary-controller 240 or at least one server 231, may result in camera 215 being activated to be ready to see and capture start-hand-washing-command 110. See FIG. 1(c) In some embodiments, start-hand-washing-command 110 may be defined-hand-gestures 116 of user 950 displayed before camera 215 (i.e. within camera 215 field of view).

For example, and without limiting the scope of the present invention, defined-hand-gestures 116 may be programmed into the software by use of a programming-camera to capture a plurality of hand gestures that may then be used to define defined-hand-gestures 116. For example, and without limiting the scope of the present invention, defined-hand-gestures 116 may be selected from one or more of the group of hand gestures comprising: holding two palms facing camera 215, holding a single thumbs up gesture before camera 215, holding two thumbs up before camera 215, and the like.

In some embodiments, the programming-camera may be camera 215. That is, camera 215 may be used by an operator as a programming-camera to capture and record hand-gestures 115, that the operator may then classify as: defined-hand-gestures 116, defined-pre-rinse-gestures 117, defined-soaping-gestures 118, defined-washing-gestures 119, and/or defined-drying-gestures 120.

In some embodiments, upon camera 215 seeing (i.e. capturing) defined-hand-gesture 116, camera 215 may record defined-hand-gesture 116 (e.g. as a start-hand-washing-command 110) as fourth-recording 114. Camera 215 may transmit fourth-recording 114 to at least one server 231 or to temporary-controller 240.

In some embodiments, start-hand-washing-command 110 may be received by temporary-controller 240 or at least one server 231 via fourth-recording 114 emanating from camera 215 or a non-recording based communication from camera 215. The software (executable by processor 332) may non-transitorily reside in memory 333. Memory 333 may be in communication with temporary-controller 240 (in which case the software may be controller-software and memory 333 may be controller-memory) or memory 333 may be in communication with at least one server 231. The software (or the controller-software) may either validate received start-hand-washing-command 110 as compliant with accepted defined-hand-gestures 116. Or the software (or the controller-software) may reject received start-hand-washing-command 110 as non-compliant with accepted defined-hand-gestures 116. In some embodiments, validation of received start-hand-washing-command 110 may result in turning on of washer 210 (e.g. with running water) for defined-first-duration 121. In some embodiments, rejection of received start-hand-washing-command 110 may result in generation of a first-error-message 126 by at least one server 231 or temporary-controller 240.

FIG. 1(*d*) may depict an exemplary embodiment a pre-rinse phase. User 950 may wet hands beneath washer 210. Such user 950 conduct may be recorded by camera 215. In some embodiments, this conduct may be validated as an appropriate pre-rinse phase. In some embodiments, during the pre-rinse phase, washer 210 may run water for defined-first-duration 121. In some embodiments, during the pre-rinse phase, camera 215 may generate first-recording 111, of user 950 wetting hands under water running from washer 210. Such hand wetting may be during defined-first-duration 121.

In some embodiments, the turning on of washer 210 for the pre-rinse phase (wetting of the hands of user 950 before receiving soap) may be initiated by: (1) user 950 placing hands in sufficient proximity of a proximity sensor of washer 210; (2) camera 215 viewing appropriate defined-pre-rinse-gestures 117; (3) user 950 placing user-transmitter 201 within sufficient distance of washer 210 to detect user-transmitter 201 (and/or for washer 210 to receive first-wireless-transmission 101 from user-transmitter 201); and/or (4) washer 210 receiving a first-turn-on-signal 131.

In some embodiments, turning on of washer 210 for the pre-rinse phase (e.g. during defined-first-duration 121) may be accomplished by at least one server 231 or temporary-controller 240 sending a first-turn-on-signal 131 to washer 210. First-turn-on-signal 131 may be received by washer 210. In some embodiments, first-turn-on-signal 131 may transverse and be communicated across a network from at least one server 231 to washer 210. The network may be a wide area network 801 (WAN 801) such as the internet, and/or a local area network (LAN).

In some embodiments, defined-first-duration 121 may be a finite time period. Defined-first-duration 121 may be predetermined by a first-value in the software. And/or defined-first-duration 121 may be set by the operator of method 100 and/or system 200 via an administrative area of an operator-graphical-user-interface (operator-GUI).

In various embodiments, washer 210 may remain on (with running water) and automatically turn off at the end of defined-first-duration 121. A reason for turning on washer 210 for defined-first-duration 121 may be to allow user 950 to wet hands prior to soaping them, to facilitate better hand washing practices, i.e. to facilitate the pre-rinse phase. In some embodiments, the steps pertaining to such pre-rinsing of the hands prior to soaping and washing may be omitted from method 100 and/or system 200, e.g. in locations where conservation of water may be deemed important (or defined-first-duration 121 may have a shortened time).

For example, and without limiting the scope of the present invention, in various embodiments defined-first-duration 121 may be 3 second, 4 seconds, 5 seconds, 6 seconds, 7 seconds, 8 seconds, 9 seconds, 10 seconds, 11 seconds, and the like. In other embodiments, other durations for defined-first-duration 121 are within the scope of this invention.

In some embodiments, the turning on and off of running water of washer 210 may be controlled merely by a proximity sensor of washer 210. When an object, e.g. user 950, may be detected by the proximity sensor a signal may cause washer 210 to release water from its faucet. When the proximity sensor may not detect any object, then no water may be related from the faucet of washer 210.

In some embodiments, the operator may be the employer or an entity controlling and/or responsible for method 100 and/or system 200. For example, and without limiting the scope of the present invention, the operator may be an agent, employee, and/or independent contractor for the employer, such as health and safety compliance officer.

In some embodiments, method 100 may comprise the step of transmitting first-recording 111 (of user 950 wetting hands under water running from washer 210) from camera 215 to at least one server 231 or temporary-controller 240. The software (or controller-software) may validate first-recording 111 as compliant with accepted defined-pre-rinse-gestures 117. Or the software (or the controller-software) may reject first-recording 111 as non-compliant with accepted defined-pre-rinse-gestures 117. Validation of first-recording 111 may result in activating soap-dispenser 221. Validation of first-recording 111 may result in the logging of a pre-rinse phase validation notation with that hand-washing-cycle 108 of that user 950. Logging of the pre-rinse phase validation may be one log entry of the plurality of individual log entries which may comprise a given hand-washing-cycle 108. Rejection of first-recording 111 may result in generation of a second-error-message 127, which may also be logged in that given hand-washing-cycle 108 of that user 950.

For example, and without limiting the scope of the present invention, defined-pre-rinse-gestures 117 may be programmed into the software by use of programming-camera to capture a plurality of pre-rinse hand gestures that may then be used to define defined-pre-rinse-gestures 117.

In some exemplary embodiments, validation of the pre-rinse phase may occur without any recordings from camera 215. In such embodiments, camera 215 may only be capturing (viewing and/or observing) hand and digit shapes and position in 3D for use against the ideal set of shapes and positions of the pattern recognition algorithm. That is, in such embodiments, camera 215 may not be capturing images of hands that may be readily deciphered by a human reviewing and/or observing an output from camera 215. In such embodiments, camera 215 may be essentially acting as a sensor that may detect shapes and positioning of hands and digits of user 950. Technically, in such embodiments, camera 215 may not even be detecting hands and digits; but rather, camera 215 may be detecting objects within its 3D field of view, i.e. shapes and positions of objects may be detected by camera 215. Such detected shapes and positions of objects, in near real-time, may then be run through the pattern recognition algorithm. The pattern recognition algorithm may ask if those observed shapes and positions of observed objects sufficiently matches the ideal set of shapes and positions for the pre-rinse phase. The ideal set of shapes and positions for the pre-rinse phase may correspond to ideal hand washing of the imaginary user 950 conducting ideal pre-rinsing (wetting) of the hands. After the comparison, the pattern recognition algorithm may cause logging of a compliant log entry or a non-compliant log entry.

In some embodiments, washer 210 may comprise a means for dispensing water 211 (e.g. the faucet), a washer-receiver, a washer-transmitter, a washer-power-source, the proximity sensor, and a means for providing feedback-signal 180 and/or completion-feedback-signal 170. The washer-receiver may be configured to receive transmissions from at least one server 231, temporary-controller 240, and user-transmitter 201. The washer-transmitter may be configured to wirelessly transmit a third-wireless-transmission 135. Wireless receiving and wireless transmission of washer 210 may be via WiFi, Bluetooth®, RFID, NFC, and the like. The washer-power-source may be configured to provide electrical power to the washer-receiver, to the washer-transmitter, and/or to the proximity sensor.

In some embodiments, method 100 may comprise the step of transmitting third-wireless-transmission 135 from washer 210, sent to at least one server 231 or to temporary-controller 240. In some embodiments, third-wireless-transmission 135 may comprise information: noting the washer is on with running water, noting the washer is off with no running water, completion of the defined-first-duration 121, and/or completion of the defined-third-duration 123.

And as noted, in some embodiments, the pre-rinse phase may be omitted or shortened.

Figure 1E:
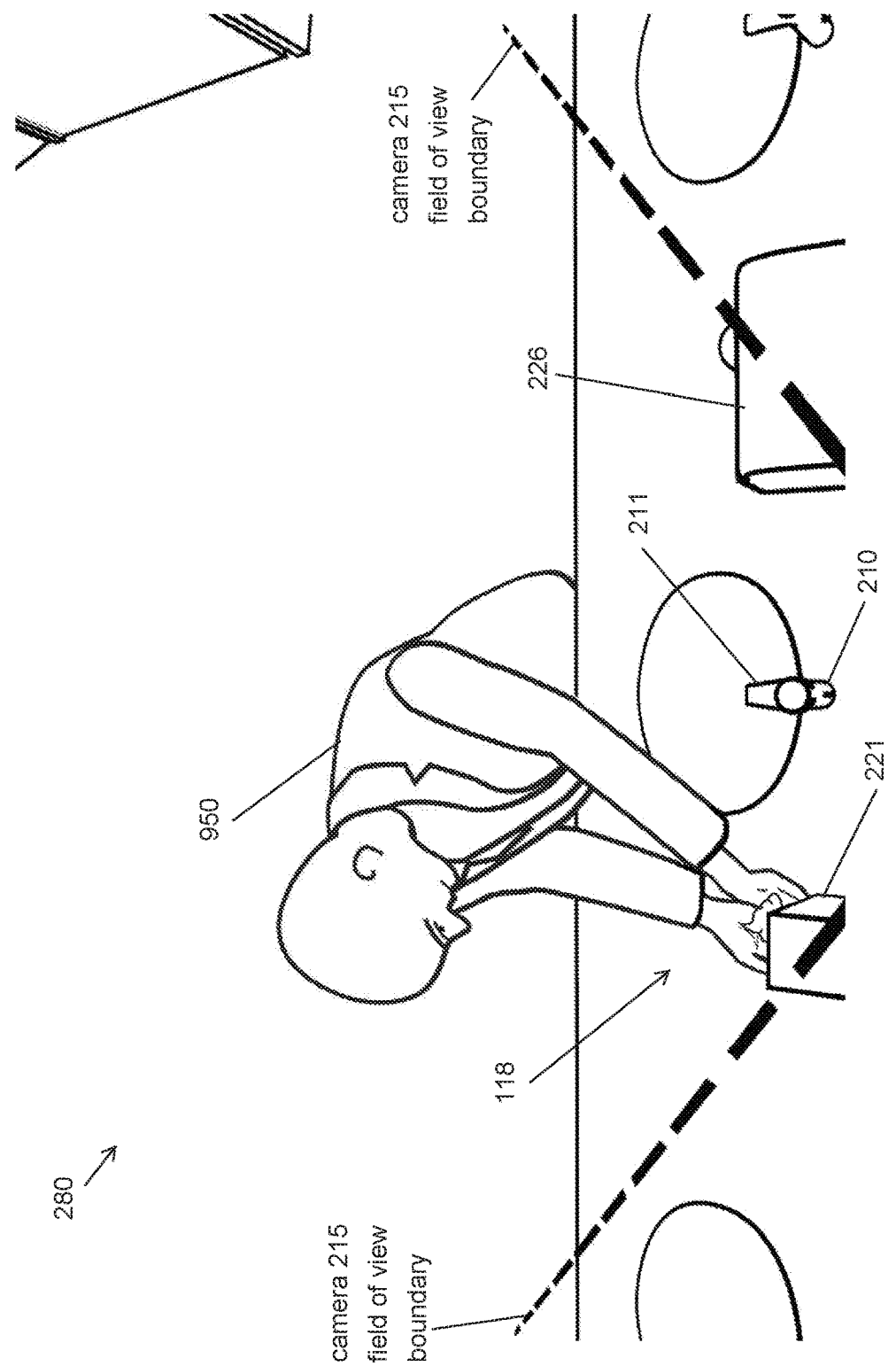
FIG. 1(e) may depict an exemplary embodiment of a soaping (i.e. lathering) phase, wherein the user receives soap that may be dispensed from a soap-dispenser, wherein this conduct data may be viewed (and sometimes recorded) by the camera and wherein this conduct data may be validated as an appropriate soaping phase.

FIG. 1(e) may depict an exemplary embodiment of the soaping (i.e. lathering) phase, wherein user 950 may receive soap that may be dispensed from soap-dispenser 221. Such user 950 conduct may be observed (or optionally recorded) by the camera 215. This conduct user 950 may be validated as an appropriate soaping phase.

In some embodiments, activation of soap-dispenser 221 may results in soap-dispenser 221 dispensing soap. Activation of soap-dispenser 221 may be triggered by either receiving a dispense-signal from a physical-proximity-sensor or by receiving first-wireless-transmission 101 from user-transmitter 201 by a soap-dispenser-receiver, if user-transmitter 201 may be sufficiently close to soap-dispenser 221. In some embodiments, sufficiently close for transmission of first-wireless-transmission 101 from user-transmitter 201 to soap-dispenser 221 may be within 10 centimeters (cm). The physical-proximity-sensor may be a component of soap-dispenser 221 (similar in design and function as the proximity sensor of washer 210). In some embodiments the sufficient proximity between the physical-proximity-sensor of soap-dispenser 221 and at least one hand of user 950 may be within 60 centimeters (cm) for activation of soap-dispenser 221. In some exemplary embodiments, that distance may be 10 or less centimeters (cm). The soap-dispenser-receiver may be a component of soap-dispenser 221.

In some embodiments, activated soap-dispenser 221 may dispense at least one metered amount of soap, upon each activation, i.e. a fixed or metered amount. In some embodiments, each activation of soap-dispenser 221 may result in a plurality of metered dispensed amounts of soap.

In various embodiments, soap-dispenser 221 may remain activated and automatically turn off at the end of defined-second-duration 122. In some embodiments, while activated, soap-dispenser 221 may continually dispense soap or continually dispense fixed bursts of soap. In some embodiments, while off, soap-dispenser 221 may not dispense soap.

In some embodiments, defined-second-duration 122 may be a finite time period. Defined-second-duration 122 may be predetermined by a second-value in the software. Defined-second-duration 122 may be a set by an operator of the method via an administrative area of operator-GUI.

For example, and without limiting the scope of the present invention, in various embodiments defined-second-duration 122 may be 3 second, 4 seconds, 5 seconds, 6 seconds, 7 seconds, 8 seconds, 9 seconds, 10 seconds, 11 seconds, and the like. In other embodiments, other durations for defined-second-duration 122 are within the scope of this invention.

In some embodiments, during the soaping phase, camera 215 may view and optionally record the soaping activities of user 950. Such soaping activities may comprise both receiving one or more bursts of soap dispensed from soap-dispenser 221 and lathering of the received soap within the hands of user 950. Recording of such soaping activities by camera 215 may be deemed second-recording 112. In some embodiments, method 100 may comprises the step of transmitting second-recording 112 from camera 215 to at least one server 231 or to temporary-controller 240.

In some embodiments, second-recording 112 may be received by at least one server 231 or temporary-controller 250. The software (or the controller-software) may validate second-recording 112 as compliant with accepted defined-soaping-gestures 118. Or the software (or the controller-software) may reject second-recording 112 as non-compliant with accepted defined-soaping-gestures 118. Validation of second-recording 112 may result in turning on washer 210 for defined-third-duration 123. Validation of second-recording 112 may result in the logging of a soaping phase validation notation with that hand-washing-cycle 108 of that user 950. Logging of the soaping phase validation may be one log entry of the plurality of individual log entries which may comprise a given hand-washing-cycle 108. Rejection of the second-recording 112 may result in generation of a third-error-message 128, which may also be logged in that given hand-washing-cycle 108 of that user 950.

For example, and without limiting the scope of the present invention, defined-soaping-gestures 118 may be programmed into the software by use of programming-camera to capture a plurality of soaping (lathering) hand gestures that may then be used to define defined-soaping-gestures 118.

In some exemplary embodiments, validation of the soaping (i.e. lathering) phase may occur without any recordings from camera 215. In such embodiments, camera 215 may only be capturing (viewing and/or observing) hand and digit shapes and position in 3D for use against the ideal set of shapes and positions of the pattern recognition algorithm. That is, in such embodiments, camera 215 may not be capturing images of hands that may be readily deciphered by a human reviewing and/or observing an output from camera 215. In such embodiments, camera 215 may be essentially acting as a sensor that may detect shapes and positioning of hands and digits of user 950. Technically, in such embodiments, camera 215 may not even be detecting hands and digits; but rather, camera 215 may be detecting objects within its 3D field of view, i.e. shapes and positions of objects may be detected by camera 215. Such detected shapes and positions of objects, in near real-time, may then be run through the pattern recognition algorithm. The pattern recognition algorithm may ask if those observed shapes and positions of observed objects sufficiently matches the ideal set of shapes and positions for the soaping phase. The ideal set of shapes and positions for the soaping phase may correspond to ideal hand washing of the imaginary user 950 conducting ideal hand soaping. After the comparison, the pattern recognition algorithm may cause logging of a compliant log entry or a non-compliant log entry. Furthermore, such non-recording validation of the soaping phase, may be facilitated by the soap comprising an ingredient which may visible from reflected IR light that may be captured by the light receiver of camera 215.

In some embodiments, soap-dispenser 221 may comprise: a means for dispensing soap, a soap-dispenser-receiver, a soap-dispenser-transmitter, a soap-dispenser-power-source, optionally a physical-proximity-sensor, and a feedback-means 290 for providing feedback-signal 180 and/or completion-feedback-signal 170. The means for dispensing soap may comprise a refillable soap reservoir, at least one dispensing valve and valve control means. The fillable soap reservoir may be in physical contact with the dispensing valve. The valve control means may be physical contact with dispensing valve. The means for dispensing soap may be configured for liquid, gel, foam, powder, and the like of various soaps and/or detergents. In some embodiments, the soap (and/or detergent) removably contained within soap-dispenser 221 may comprise an ingredient (e.g. a dye) that may make the soap visible to reflected light off of the soap to the light sensor. Such an ingredient may be visible from reflected IR light.

In some embodiments, the soap-dispenser-receiver may be configured to receive transmissions from at least one server 231, temporary-controller 240, and user-transmitter 201. The soap-dispenser-transmitter may be configured to wirelessly transmit a fourth-wireless-transmission 140. Wireless receiving and wireless transmission of soap-dispenser 221 may be via WiFi, Bluetooth®, RFID, NFC, and the like. The soap-dispenser-power-source may be configured to provide electrical power to the soap-dispenser-receiver, to the soap-dispenser-transmitter, and to the physical-proximity-sensor.

In some embodiments, method 100 may comprise the step of transmitting fourth-wireless-transmission 140 from soap-dispenser 221, and sent to at least one server 231 or temporary-controller 240.

In some embodiments, fourth-wireless-transmission 140 may comprise information: noting soap-dispenser 221 is on and/or activated; noting soap-dispenser 221 may be off and/or not-activated; and/or completion of defined-second-duration 122. Such information may also comprise date and time information.

FIG. 1(f) may depict an exemplary embodiment the rinse (washing) phase. In the rinse phase user 950 may rinses hands of soap from beneath washer 210. Such user 950 conduct may be recorded by camera 215. This user 950 conduct may be validated as an appropriate rinse phase.

In some embodiments, the turning on of washer 210 with running water for the rinse phase (rinsing of soap from the hands of user 950) may be initiated by: (1) user 950 placing hands in sufficient proximity of the proximity sensor of washer 210; (2) camera 215 viewing appropriate defined-washing-gestures 119; (3) user 950 placing user-transmitter 201 within sufficient distance of washer 210 to detect user-transmitter 201 (and/or for washer 210 to receive first-wireless-transmission 101 from user-transmitter 201); and/or (4) washer 210 receiving a second-turn-on-signal 132.

In some embodiments, the turning on of washer 210 with running water for defined-third-duration 123 may be accomplished by at least one server 231 or temporary-server 240 sending second-turn-on-signal 132 to washer 210. Second-turn-on-signal 132 may be received by washer 210. Turning on washer 210 for defined-third-duration 123 may be accomplished by at least one server 231 or temporary-controller 240 sending second-turn-on-signal 132 to washer 210. Second-turn-on-signal 132 may transverse and be communicated across the network from at least one server 231 to washer 240. The network may be a WAN 801 such as the internet, and/or a LAN.

In some embodiments, defined-third-duration 123 may be a finite time period. Defined-third-duration 123 may be predetermined by a third-value in the software. Or defined-third-duration 123 may be set by the operator of the method via an administrative area of an operator-GUI.

In various embodiments, washer 210 may remain on (with running water) and automatically turn off at the end of defined-third-duration 123. A reason for turning on washer 210 for defined-third-duration 123 may be to allow user 950 to wash and rinse hands of soap.

For example, and without limiting the scope of the present invention, in various embodiments defined-third-duration 123 may be 9 second, 10 seconds, 15 seconds, 20 seconds, 25 seconds, 30 seconds, 45 seconds, 60 seconds, and the like. In other embodiments, other durations for defined-third-duration 123 are within the scope of this invention.

In some embodiments, during the rinse phase, camera 215 may view and record the rinsing activities of user 950. Such rinsing activities may comprise using water from washer 210 to rinse soap from the hands of user 950. Recording of such soaping activities by camera 215 may be deemed third-recording 113. In some embodiments, method 100 may comprises the step of transmitting third-recording 113 from camera 215 to at least one server 231 or to temporary-controller 240.

In some embodiments, when washer 210 may be operating during the rinse phase (e.g. possibly during defined-third-duration 123) or during the pre-rinse phase, washer 210 may output (i.e. dispenses) warm water. In such embodiments, camera 215 may comprise thermal-imaging-optics, such that third-recording 113 may comprise thermal images of warm water in contact with the hands of user 950. The digital-optics of camera 215 may comprise thermal-imaging-optics.

In some embodiments, third-recording 113 may be received by at least one server 231 or temporary-controller 250. The software (or the controller-software) may validate third-recording 113 as compliant with accepted defined-washing-gestures 119. Or the software (or the controller-software) may reject third-recording 113 as non-compliant with accepted defined-washing-gestures 119. Validation of third-recording 113 may result in the logging of an event. Validation of third-recording 113 may result in the logging of a rinse phase validation notation with that hand-washing-cycle 108 of that user 950. Logging of the rinse phase validation may be one log entry of the plurality of individual log entries which may comprise a given hand-washing-cycle 108. Rejection of the third-recording 113 may result in generation of a fourth-error-message 129, which may also be logged in that given hand-washing-cycle 108 of that user 950.

For example, and without limiting the scope of the present invention, the defined-washing-gestures 119 may be programmed into the software by use of programming-camera to capture a plurality of hand washing and rinsing gestures that may then be used to define defined-washing-gestures 119. In embodiments, where the digital-optics of camera 215 may comprise thermal-imaging-optics, then defined-washing-gestures 119 may include a requirement for capturing thermal images of increased temperatures of the hands' surfaces. Note, in some embodiments the gestures comprising defined-washing-gestures 119 may be substantially the same gestures which may comprise defined-pre-rinse-gestures 117.

In embodiments, employing warm water, validating the rinse phase may include checking for the presence of warm water on the hands of user 950, by use of camera 215. Validation of the third-recording 113 as compliant by the software (or controller-software) may involve the software (or controller-software) detecting accepted defined-washing-gestures 119 and thermal images of increased temperatures of the hands' surfaces. Rejection of third-recording 113 as non-compliant by the software (or controller-software) may involve the software (or controller-software) not detecting accepted defined-washing-gestures 119, and/or not detecting increased temperatures of the hands' surfaces. Rejection of third-recording 113 when a problem may be with not detecting increased temperatures of the hands' surfaces may result in generation of a fifth-error-message 130, which may also be logged in that given hand-washing-cycle 108 of that user 950.

In some embodiments, fifth-error-message 130 may denote that an increase in user's hands was not detected during the rinse phase (e.g. during defined-third-duration 123). Such a message may provide notice to the operator of a potential maintenance issue with respect to washer 210 supplying warm water and/or a problem in the thermal-imaging-optics.

In some exemplary embodiments, validation of the rinse (washing) phase may occur without any recordings from camera 215. In such embodiments, camera 215 may only be capturing (viewing and/or observing) hand and digit shapes and position in 3D for use against the ideal set of shapes and positions of the pattern recognition algorithm. That is, in such embodiments, camera 215 may not be capturing images of hands that may be readily deciphered by a human reviewing and/or observing an output from camera 215. In such embodiments, camera 215 may be essentially acting as a sensor that may detect shapes and positioning of hands and digits of user 950. Technically, in such embodiments, camera 215 may not even be detecting hands and digits; but rather, camera 215 may be detecting objects within its 3D field of view, i.e. shapes and positions of objects may be detected by camera 215. Such detected shapes and positions of objects, in near real-time, may then be run through the pattern recognition algorithm. The pattern recognition algorithm may ask (compare) if those observed shapes and positions of observed objects sufficiently matches the ideal set of shapes and positions for the rinse phase. The ideal set of shapes and positions for the rinse phase may correspond to ideal hand rinsing of the imaginary user 950 conducting ideal hand rinsing. After the comparison, the pattern recognition algorithm may cause logging of a compliant log entry or a non-compliant log entry. Furthermore, such non-recording validation of the rinse phase, may be facilitated by the soap comprising the ingredient which may be visible from reflected IR light that may be captured by the light receiver of camera 215, such that camera 215 may be used detect no or minimal amounts of the ingredient, which may then indicate that the ingredient has been washed off.

In some embodiments, logging of the event within memory 333 in communication with the at least one server 231 or temporary-controller 240 may result in: (1) completion of the given hand-washing-cycle 108, see FIG. 1(g) discussion below; (2) a validate-entire-cycle-command, see FIG. 1(g) discussion below; or (3) initiation of the drying phase, see FIG. (f) discussion below. That is, the event may be a node, wherein depending upon a given embodiment, once method 100 may reach the event, method 100 may then progress via different subsequent steps. For example, and without limiting the scope of the present invention, in embodiments which may not include a drying phase, when method 100 may reach the event, method 100 may validate the entire hand-washing-cycle 108 and/or may terminate/complete that given hand-washing-cycle 108.

Figure 1G:
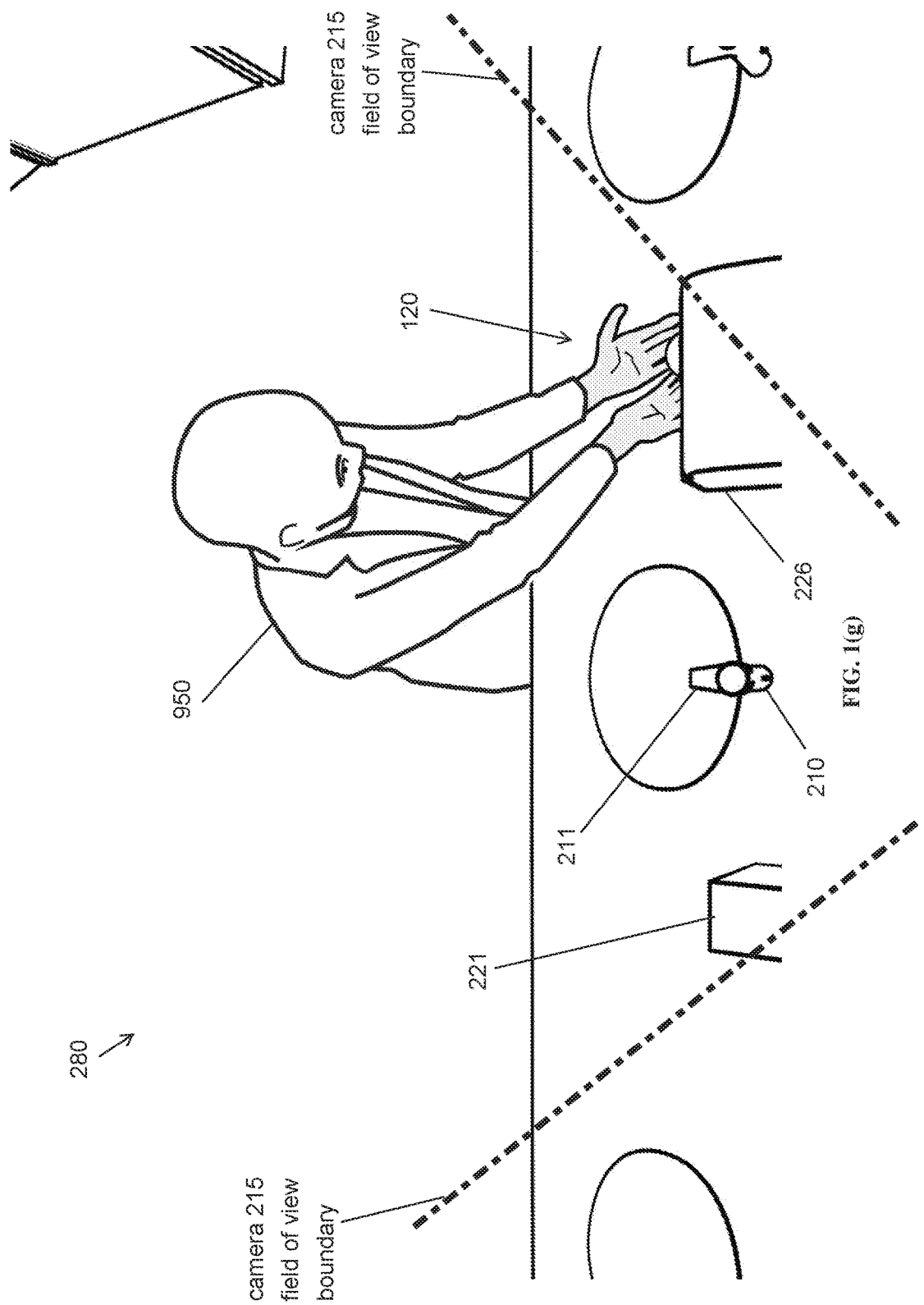
FIG. 1(g) may depict an exemplary embodiment of a drying phase, wherein the user dries hands of water and/or moisture from a hand-dryer, wherein this conduct data may be viewed (and sometimes recorded) by the camera and wherein this conduct data may be validated as an appropriate drying phase.

FIG. 1(g) may depict an exemplary embodiment of the drying phase. User 950 may dry hands of water and/or of moisture from hand-dryer 226. Such user 950 conduct may be recorded by camera 215. This user 950 conduct may be validated as an appropriate drying phase. In some embodiments, hand-dryer 226 may comprise a feedback-means 290 for providing feedback-signal 180 and/or completion-feedback-signal 170.

In some embodiments, the turning on of hand-dryer 226 for the drying phase (drying of the hands of user 950) may be initiated by: (1) user 950 placing hands in sufficient proximity of a proximity-sensor of hand-dryer 226; (2) camera 215 viewing appropriate defined-drying-gestures 120; (3) user 950 placing user-transmitter 201 within sufficient distance of hand-dryer 226 to detect user-transmitter 201 (and/or for hand-dryer 226 to receive first-wireless-transmission 101 from user-transmitter 201); and/or (4) hand-dryer 226 receiving a third-turn-on-signal 145. In some embodiments, turning on of hand-dryer 226 may result in activation of hand-dryer 226. In some embodiments, the activation of hand-dryer 226 may result in hand-dryer 226 providing a means-to-dry-hands. In some embodiments the sufficient proximity between the proximity-sensor of hand-dryer 226 and at least one hand of user 950 may be within 60 centimeters (cm) for activation of hand-dryer 226. In some exemplary embodiments, that distance may be 10 or less centimeters (cm). In some embodiments, after user 950 may have completed drying of the hands, user 950 may need to leave hand-washing-compliance area 280 within a set time; otherwise, method 100 and/or system 200 may prompt user 950 to repeat a hand washing cycle. The set time may be set by the operator in some embodiments. For example, and without limiting the scope of the present invention, the set time may be one minute.

In some embodiments, the means-to-dry-hands may comprise a device which may blow air over the hands to dry them (see e.g., FIG. 1(g)) and/or a device which may dispense one or more towels or a device which may make available one or more towels to the user.

In some embodiments, when hand-dryer 226 may be activated, hand-dryer 226 may operate for a defined-fifth-duration 125. In some embodiments, defined-fifth-duration 125 may be a finite time period. Defined-fifth-duration 125 may be predetermined by a fifth-value in the software. Defined-fifth-duration 125 may be set by an operator of the method via an administrative area of operator-GUI. In various embodiments, hand-dryer 226 may remain on and active, and automatically turn off at the end of defined-fifth-duration 125.

For example, and without limiting the scope of the present invention, in various embodiments defined-fifth-duration 125 may be 5 seconds, 10 seconds, 15 seconds, 20 seconds, 25 seconds, 30 seconds, 35 seconds, and the like. In other embodiments, other durations for defined-fifth-duration 125 are within the scope of this invention.

In some embodiments, hand-dryer 226 may comprise the means-to-dry-hands, a hand-dryer-receiver, a hand-dryer-transmitter, a hand-dryer-power-source, and the proximity-sensor. The hand-dryer-receiver may be configured to receive transmissions from at least one server 231, temporary-controller 240, and user-transmitter 201. The hand-dryer-transmitter may be configured to wirelessly transmit a fifth-wireless-transmission 150. Wireless receiving and wireless transmission of hand-dryer 226 may be via WiFi, Bluetooth®, RFID, NFC, and the like. The hand-dryer-power-source is configured to provide electrical power to the hand-dryer-receiver, to the hand-dryer-transmitter, and to the proximity-sensor of hand-dryer 226.

In some embodiments, method 100 may comprise the step of transmitting fifth-wireless-transmission 150 from hand-dryer 226 and sent to at least one server 231 or to temporary-controller 240. In some embodiments, fifth-wireless-transmission 150 may comprise information: noting hand-dryer 226 is on and activated, noting hand-dryer 226 is off, and/or completion of defined-fifth-duration 125.

In some embodiments, during the drying phase, camera 215 may view and record the drying activities of user 950. Such drying activities may comprise user 950 drying hands with an air blower or with provided towels, depending upon which embodiment of the means-to-dry-hands may be employed. Recording of such drying activities by camera 215 may be deemed fifth-recording 155. In some embodiments, method 100 may comprises the step of transmitting fifth-recording 155 from camera 215 to at least one server 231 or to temporary-controller 240.

In some embodiments, fifth-recording 155 may be received by at least one server 231 or temporary-controller 250. The software (or the controller-software) may validate fifth-recording 155 as compliant with accepted defined-drying-gestures 120. Or the software (or the controller-software) may reject fifth-recording 155 as non-compliant with accepted defined-drying-gestures 120. Validation of fifth-recording 155 may result in the logging of a drying phase validation notation with that hand-washing-cycle 108 of that user 950. Logging of the soaping phase validation may be one log entry of the plurality of individual log entries which may comprise a given hand-washing-cycle 108. Rejection of the fifth-recording 155 may result in generation of a sixth-error-message 160, which may also be logged in that given hand-washing-cycle 108 of that user 950.

For example, and without limiting the scope of the present invention, defined-drying-gestures 120 may be programmed into the software by use of programming-camera to capture a plurality of drying hand gestures that may then be used to define defined-drying-gestures 120.

In some exemplary embodiments, validation of the drying phase may occur without any recordings from camera 215. In such embodiments, camera 215 may only be capturing (viewing and/or observing) hand and digit shapes and position in 3D for use against the ideal set of shapes and positions of the pattern recognition algorithm. That is, in such embodiments, camera 215 may not be capturing images of hands that may be readily deciphered by a human reviewing and/or observing an output from camera 215. In such embodiments, camera 215 may be essentially acting as a sensor that may detect shapes and positioning of hands and digits of user 950. Technically, in such embodiments, camera 215 may not even be detecting hands and digits; but rather, camera 215 may be detecting objects within its 3D field of view, i.e. shapes and positions of objects may be detected by camera 215. Such detected shapes and positions of objects, in near real-time, may then be run through the pattern recognition algorithm. The pattern recognition algorithm may ask (compare) if those observed shapes and positions of observed objects sufficiently matches the ideal set of shapes and positions for the drying phase. The ideal set of shapes and positions for the drying phase may correspond to ideal hand drying of the imaginary user 950 conducting ideal hand drying. After the comparison, the pattern recognition algorithm may cause logging of a compliant log entry or a non-compliant log entry.

Figure 1H:
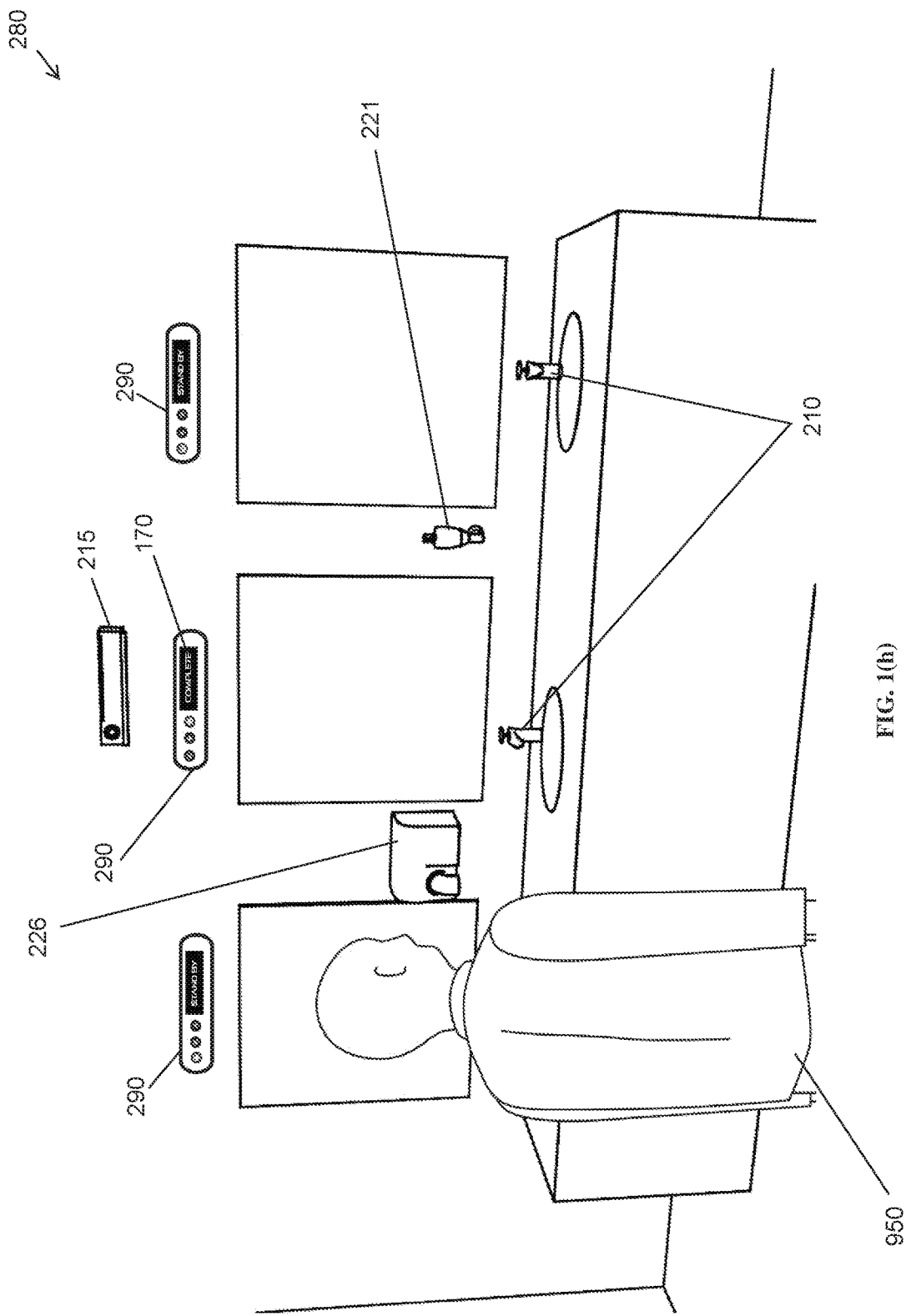
FIG. 1(h) may depict an exemplary embodiment of the user receiving a completion-feedback-signal which may notify the user that the given hand-washing-cycle may have terminated and/or that the given hand-washing-cycle may have terminated successfully, with the user in compliance.

FIG. 1(h) may depict an exemplary embodiment of user 950 receiving a completion-feedback-signal 170 which may notify user 950 that the given hand-washing-cycle 108 may have terminated and/or that the given hand-washing-cycle 108 may have terminated successfully, with user 950 in proper hand washing compliance.

In some embodiments, logging of the event may trigger transmission of the hand-washing-cycle-completion-signal 165 to one or more of various target devices because the hand-washing-cycle 108 may have completed.

In some embodiments, transmission of the hand-washing-cycle-completion-signal 165 may emanate from at least one server 231 or temporary-controller 240. A target device of the hand-washing-cycle-completion-signal may be one or more of the group comprising: user-transmitter 201, entry-sensor 206, washer 210, soap-dispenser 221, camera 215, hand-dryer 226, wireless-router 250, temporary-controller 240, operator-computing-device 260, user-computing device 270, and the like. The target device may be configured to receive the hand-washing-cycle-completion-signal 165. Upon receipt of the hand-washing-cycle-completion-signal 165, the target device(s) may emit a completion-feedback-signal 170. In some embodiments, the completion-feedback-signal 170 may be visual and/or audible, such that user 950 may notice completion-feedback-signal 170.

For example, and without limiting the scope of the present invention, entry-sensor 206, washer 210, soap-dispenser 221, camera 215, hand-dryer 226 (if present) may all substantially simultaneously emit a beep and/or flash of a green LED (light emitting diode) to communicate an end to that given hand-washing-cycle 108. In some embodiments, at least one server 231 or temporary-controller 240 may cause a notification signal to be sent and viewable by user-computing-device 270 noting the end to that given hand-washing-cycle 108. In some embodiments, at least one server 231 or temporary-controller 240 may cause a notification signal to be sent and viewable by operator-computing-device 260 noting the end to that given hand-washing-cycle 108.

In some embodiments, logging of the event may comprise inclusion of the following information: date of completion of the hand-washing-cycle 108, time of completion of the hand-washing-cycle 108, and information contained within the first-wireless-transmission 101 (e.g. unique-user-ID 103, user's name, and/or user's job title).

In some embodiments, upon at least one server 231 or temporary-controller 240 receiving the event, when the event corresponds to an end of a given hand-washing-cycle 108, at least one server 231 or temporary-controller 240 may cause transmission of hand-washing-cycle-completion-signal 165 to the various target devices. One or more of the target devices may then emit completion-feedback-signal 170.

In some embodiments, method 100 may comprise the step of receiving a validate-entire-cycle-command 175. Validate-entire-cycle-command 175 may be embedded within the event. Receipt of validate-entire-cycle-command 175 may cause the software (or controller-software) to check each log entry for a given hand-washing-cycle 108 for any error message entries and/or other log entries that demonstrate a problem in the given hand-washing-cycle 108. If the software (or controller-software) finds no error message entries and/or no log entries demonstrating a problem in the given hand-washing-cycle 108, then the software (or controller-software) may cause a final-overall-validation-message 176 to be logged into that hand-washing-cycle 108. Or if the software (or controller-software) finds at least one error message entry or at least one log entry demonstrating a problem in the given hand-washing-cycle 108, then the software (or controller-software) may cause an operator-review-notification 177 message to be transmitted to the operator (e.g. in an email and/or text message). Operator-review-notification 177 may request review by the operator of the given hand-washing-cycle 108.

In some embodiments, the software (or controller-software) finding a potential problem with a given hand-washing-cycle 108 may also result in a notification sent to user 950 and viewable by user-computing-device 270, so user 950 may be timely notified of the potential problem, as user 950 may have a fresh memory of any potential problems.

In some embodiments, method 100 may comprise the step of transmitting a feedback-signal 180 to user 950 from feedback-means 290. In some embodiments, feedback-signal 180 may be of a nature of general feedback from any phase and any target device; whereas completion-feedback-signal 170, may be for feedback at the end of a given hand-washing-cycle 108. The transmitted feedback-signal 180 may be selected from emitting from one or more feedback-means 290 in physical contact with one or more of the group comprising: user-transmitter 201, entry-sensor 206, camera 215, washer 210, soap-dispenser 221, hand-dryer 226, the temporary-controller 240, user-computing-device 270, and the like.

For example, and without limiting the scope of the present invention, the entry-sensor 206 may flash a green LED and/or a beep to indicate to user 950 that entry-sensor 206 has received first-wireless-transmission 101. Or for example, and without limiting the scope of the present invention, entry-sensor 206 may flash a red LED and/or a buzzer sound to indicate to user 950 that entry-sensor 206 has not correctly received first-wireless-transmission 101 or that entry-sensor 206 may be experiencing an error.

For example, and without limiting the scope of the present invention, camera 215 may flash a green LED and/or a beep to indicate to user 950 that any of fourth-recording 114, first-recording 111, second-recording 112, third-recording 113, and/or fifth-recording 155 were successfully validated or successfully transmitted to at least one server 231 or to temporary-controller 240. Or for example, and without limiting the scope of the present invention, the camera 215 may flash a red LED and/or emit a buzzer sound to indicate to user 950 that any of fourth-recording 114, first-recording 111, second-recording 112, third-recording 113, and/or fifth-recording 155 were not successfully validated or not successfully transmitted.

For example, and without limiting the scope of the present invention, washer 210 may flash a green LED and/or a beep to indicate to user 950 that water may be running from the faucet of washer 210.

For example, and without limiting the scope of the present invention, the soap-dispenser 221 may flash a green LED and/or a beep to indicate that soap-dispenser 221 may be dispensing soap. Or for example, and without limiting the scope of the present invention, the soap-dispenser 221 may flash a red LED and/or emit a buzzer sound to indicate that soap-dispenser 221 may be low our out of soap in its soap reservoir.

In some embodiments, feedback-signal 180 may be in a form of an audible signal and/or a visual signal from feedback-means 290. The audible signal may be one or more beeps, one or more buzzer sounds, or a sound from a sound-file provided by the operator and received by at least one server 231. The visual signal may be lighting from one or more lights, lighting from one or more lights of at least two different colors, or flashing at least one light on and off. The light may be from a light source such as a LED.

In some embodiments, feedback-signal 180 may be transmitted for a defined-fourth-duration 124. In some embodiments, defined-fourth-duration 124 may be a finite time period. Defined-fourth-duration 124 may be predetermined by a fourth-value in the software (controller-software). Or defined-fourth-duration 124 may be set by the operator via an administrative area of an operator-GUI. In various embodiments, signal-feedback 180 may remain transmitting and automatically turn off at the end of defined-fourth-duration 124.

For example, and without limiting the scope of the present invention, in various embodiments defined-fourth-duration 124 may be 3 second, 4 seconds, 5 seconds, 6 seconds, 7 seconds, 8 seconds, 9 seconds, 10 seconds, 11 seconds, and the like. In other embodiments, other durations for defined-fourth-duration 124 are within the scope of this invention.

FIG. 2 may depict an exemplary embodiment of a system 200 for user hand washing compliance. Some components of such system 200 may be depicted, with some potential communication relationships of these system components. Some of these system 200 components have been introduced above when discussing method 100 in discussing the FIG. 1 series of figures.

With respect to FIG. 2, in some embodiments, system 200 may comprise user-transmitter 201, entry-sensor 206, washer 210, camera 215, soap-dispenser 221, hand-dryer 226, temporary-controller 240, wireless-router 250, wide area network (WAN) 801, at least one server 231, operator-computing-device 260, user-computing-device 270, and the like. In some embodiments, system 200 may also include user 950, the operator, or both user 950 and the operator.

In some embodiments, user-transmitter 201 may be integral to the wrist-band 202 or the identification-card 203. When user-transmitter 201 may be used in method 100 for hand washing compliance of user 950, user-transmitter 201 may generally be associated (maintained) with user 950. In some embodiments, user-transmitter 201 may comprise the Wireless-transmitter 404. Wireless-transmitter 404 may wirelessly transmit first-wireless-transmission 101. As noted in method 100, first-wireless-transmission 101 may be sent to and target various target devices, including entry-sensor 206, at least one server 231, temporary-controller 240, entry-sensor 206, washer 210, camera 215, hand-dryer 226, wireless-router 250, operator-computing-device 260, user-computing-device 270, and the like.

In some embodiments, wireless-transmitter 404 may be configured for wireless transmission using a wireless communication protocol selected from one or more of the group comprising: Bluetooth®, WiFi, RFID, NFC, and the like.

In some embodiments, user-transmitter 201 may comprise wireless-receiver 405. In some embodiments, wireless-receiver 405 may be configured for receiving wireless transmissions using one or more wireless communication protocols selected from the group comprising: Bluetooth®, WiFi, RFID, NFC, and the like. In some embodiments, wireless-receiver 405 may be configured for receiving wireless transmissions from one or more of at least one server 231, temporary-controller 240, entry-sensor 206, washer 210, camera 215, hand-dryer 226, wireless-router 250, operator-computing-device 260, user-computing-device 270, and the like.

In some embodiments, wireless-transmitter 404 and/or wireless-receiver 405 may be a wireless antenna of user-transmitter 201.

In some embodiments, the information comprising first-wireless-transmission 101 may be stored in user-memory 406. That is, user-transmitter 201 may comprise user-memory 406. User-memory 406 may be in physical contact with wireless-transmitter 404 and/or wireless-receiver 405. In some embodiments, user-memory 406 may be read-only. In some embodiments, user-memory 406 may be rewritable.

In some embodiments, user-transmitter 201 may comprise optional-processor 409, user-memory 406, antenna 404/405, optional-function-chip 407, feedback-means 290, battery 410, and the like. See FIG. 4. In embodiments, which contain optional-function-chip 407, optional-processor 409 may also be present to control user-transmitter 201. optional-function-chip 407 may comprise such functions as the heartbeat sensor, vibration detector, and/or accelerometer. Battery 410 may be rechargeable.

In some embodiments, entry-sensor 206 may be located at least one access point (e.g. entrance 281) to hand-washing-compliance-area 280. Entry-sensor 206 may comprise the sensor-receiver, the sensor-transmitter, the sensor-power-source, and the means for providing feedback-signal 180 and/or completion-feedback-signal 170. The sensor-receiver may be configured to receive first-wireless-transmission 101. In some embodiments, the sensor-receiver may be configured to receive wireless transmission from at least one server 231 (or temporary-controller 240). The sensor-transmitter may be configured to wirelessly transmit second-wireless-transmission 106. The sensor-power-source may be configured to provide electrical power to the sensor-receiver, to the sensor-transmitter the means for providing feedback-signal 180 and/or completion-feedback-signal 170.

In some embodiments, washer 210 may comprise the means for dispensing water 211 (e.g. the faucet), the washer-receiver, the washer-transmitter, the washer-power-source, optionally the proximity sensor, and the means for providing feedback-signal 180 and/or completion-feedback-signal 170. The washer-receiver may be configured to receive transmissions from at least one server 231 (or temporary-controller 240) and/or the user-transmitter 201. The washer-transmitter may be configured to wirelessly transmit third-wireless-transmission 135. The washer-power-source may be configured to provide electrical power to the washer-receiver, to the washer-transmitter, the proximity sensor, and to the means for providing feedback-signal 180 and/or completion-feedback-signal 170.

In general see camera 215 discussion above under the FIG. 1(c) and FIG. 5 discussion above. In some embodiments, camera 215 may comprise digital-optics, a camera-receiver, a camera-transmitter, a camera-power-source, a camera-memory, a camera-processor, and a means for providing feedback-signal 180 and/or completion-feedback-signal 170.

In some embodiments, the digital-optics may comprise at least one adjustable lens. In some embodiments, the digital-optics of camera 215 may also comprise thermal-imaging-optics. In some embodiments, the digital-optics may comprise camera-software (i.e. camera-firmware). The camera-software may instruct the camera-processor how to process images received by the at least one adjustable lens. The camera-software may be non-transitorily stored within the camera-memory. Together, the camera-software, the camera-processor, the at least one adjustable lens, and the camera-memory may permit camera 215 to capture (view), record, and recognize: (1) user 950 gestures, including hand-gestures; (2) stereoscopic events of where in three-dimensional space user 950 gesture may have occurred; and/or (3) thermal images, e.g. of warm or cold water.

In some embodiments, the camera-receiver may be configured to receive transmissions from at least one server 231, temporary-controller 240, user-transmitter 201, entry-sensor 206, washer 210, soap-dispenser 221, hand-dryer 226, operator-computing-device 260, user-computing device 270, and the like.

In some embodiments, the camera-transmitter may be configured to wirelessly transmit first-recording 111, second-recording 112, third-recording 113, fourth-recording 114, and other recordings. First-recording 111, second-recording 112, third-recording 113 and any other recording from camera 215 may be transmitted to temporary-controller 240 and/or to at least one server 231.

For example, and without limiting the scope of the present invention, in some embodiments, the camera-transmitter may be configured to wirelessly transmit fourth-recording 114. Upon camera 215 seeing (viewing) defined-hand-gesture 116, camera 215 may record defined-hand-gesture 116 as fourth-recording 114. Camera 215 may transmit fourth-recording 114 to at least one server 231 or to temporary-controller 240.

In some embodiments, the camera-power-source may be configured to provide electrical power to: the digital-optics, the camera-receiver, the camera-transmitter, the camera-memory, the camera-processor, the means for providing feedback-signal 180 and/or completion-feedback-signal 170.

In some embodiments, soap-dispenser 221 may comprise: a means for dispensing soap, a soap-dispenser-receiver, a soap-dispenser-transmitter, a soap-dispenser-power-source, optionally a physical-proximity-sensor, and a means for providing feedback-signal 180 and/or completion-feedback-signal 170. The means for dispensing soap may comprise a refillable soap reservoir, at least one dispensing valve and valve control means. The fillable soap reservoir may be in physical contact with the dispensing valve. The valve control means may be physical contact with dispensing valve. The means for dispensing soap may be configured for liquid, gel, foam, powder, and the like of various soaps and/or detergents. The soap-dispenser-receiver may be configured to receive transmissions from at least one server 231, temporary-controller 240, and user-transmitter 201. The soap-dispenser-transmitter may be configured to wirelessly transmit a fourth-wireless-transmission 140. Wireless receiving and wireless transmission of soap-dispenser 221 may be via WiFi, Bluetooth®, RFID, NFC, and the like. The soap-dispenser-power-source may be configured to provide electrical power to the soap-dispenser-receiver, to the soap-dispenser-transmitter, and to the physical-proximity-sensor.

Figure 3:
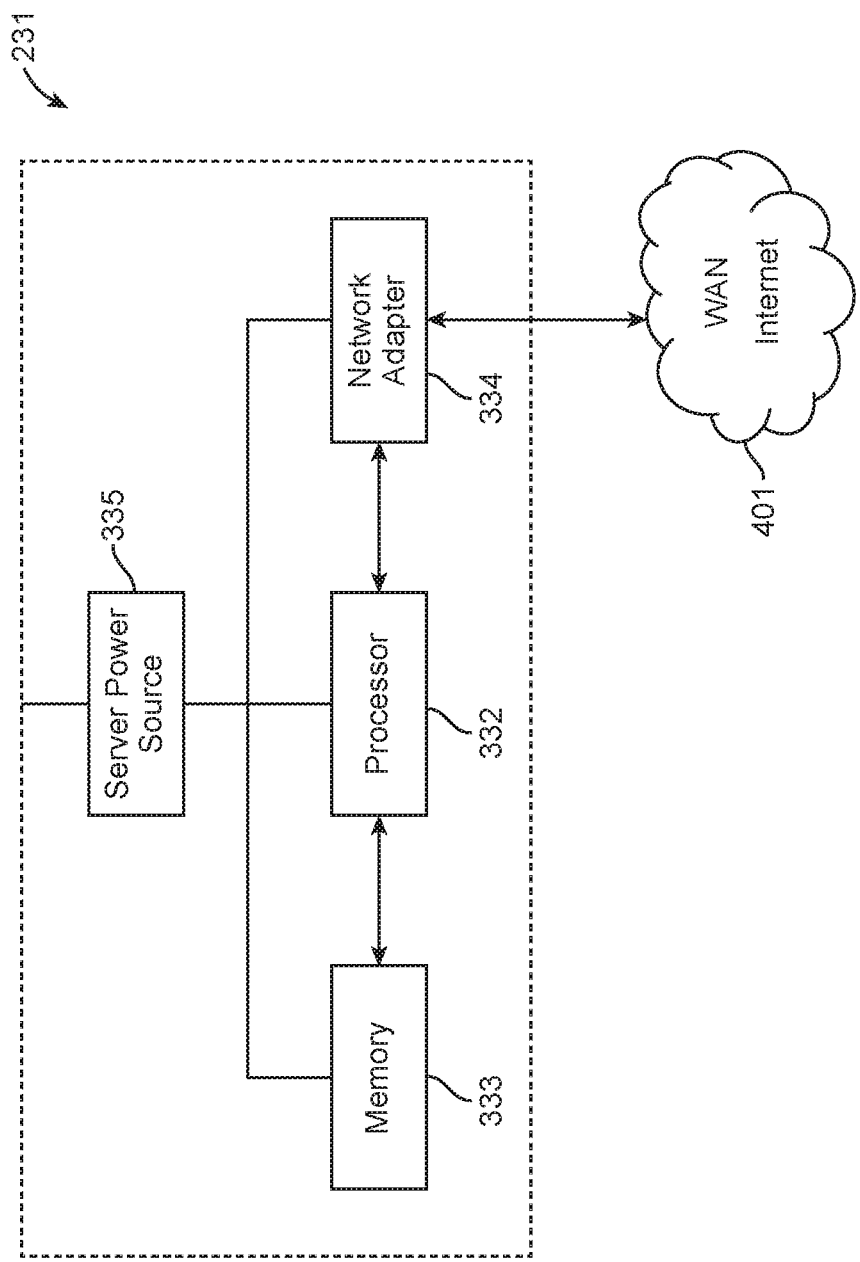
FIG. 3 may depict exemplary subcomponents of at least one server in a block diagram format. This block diagram may also depict how the subcomponents of a temporary-controller may be structured.

Note, at least one server 231 and temporary-controller 240 are discussed under the FIG. 3 discussion.

Continuing discussing FIG. 2, in terms of system component functionality, in some embodiments as noted above in method 100, receipt of first-wireless-transmission 101 by the sensor-entry 206 may initiate transmission of second-wireless-transmission 106 by sensor-entry 206. In some embodiments, second-wireless-transmission 106 may comprise information logging initiation of a given hand-washing-cycle 108 in user-hand-washing-log 107. Hand-washing-cycle 108 may comprise at least one log entry pertaining to a given user's 950 interactions with system 200 components. User-hand-washing-log 107 may be the database. The database may be maintained in memory 333.

In some embodiments, third-wireless-transmission 135 may comprise information: noting the washer 210 may be on with running water, noting washer 210 may be off with no running water, noting completion of defined-first-duration 121, and/or noting completion of a defined-third-duration 123. In some embodiments, fourth-wireless-transmission 140 may comprise information: noting soap-dispenser 221 may be on and activated, noting soap-dispenser 221 may be off, and/or completion of defined-second-duration 122.

In some embodiments, first-recording 111 may be of user 950 wetting hands under water running from washer 210 during the pre-rinse phase (possibly during defined-first-duration 121). In some embodiments, second-recording 112 may be of user 950 receiving soap from soap-dispenser 221. In some embodiments, third-recording 113 may be of user 950 washing and subsequently rinsing the soap from the hands of user 950 during the rinse phase (possibly during defined-third-duration 123).

Depending upon if the embodiment concludes with the rinse phase or drying phase, initiation of the completion phase may involve at least one server 231 (or temporary-controller 240) transmitting hand-washing-cycle-completion-signal 165 to one or more of the target devices. The target devices may include: user-transmitter 201, entry-sensor 206, washer 210, camera 215, soap-dispenser 221, hand-dryer 226, and the like. Receipt of hand-washing-cycle-completion-signal 165 by one or more of the target devices may results in a completion-feedback-signal 170 being broadcast to user 950 from one or more of the target devices.

In some embodiments, hand-dryer 226 may comprise the means-to-dry-hands, the hand-dryer-receiver, the hand-dryer-transmitter, the proximity-sensor, the hand-dryer-power-source, and a means for providing feedback-signal 180 and/or completion-feedback-signal 170. In some embodiments, the means-to-dry-hands may comprise a device which may blow air over the hands to dry them and/or a device which may dispense one or more towels or a device which may make available one or more towels to the user. The hand-dryer-receiver may be configured to receive transmissions from at least one server 231 (temporary-controller 240) and/or user-transmitter 201. The hand-dryer-transmitter may be configured to wirelessly transmit fifth-wireless-transmission 150. Wireless receiving and wireless transmission of hand-dryer 226 may be via WiFi, Bluetooth®, RFID, NFC, and the like. Fifth-wireless-transmission 150 may comprise information: noting hand-dryer 226 may be on and activated, noting hand-dryer 226 may be off, and/or noting completion of defined-fifth-duration 125. The hand-dryer-power-source may be configured to provide electrical power to the means-to-dry-hands, the hand-dryer-receiver, the hand-dryer-transmitter, the proximity-sensor, and the means for providing feedback-signal 180 and/or completion-feedback-signal 170.

In some embodiments, wireless-router 250 may be in wireless communication with one or more of the group comprising: user-transmitter 201, entry-sensor 206, washer 210, soap-dispenser 221, camera 215, hand-dryer 226, WAN 801, a LAN, at least one server 231, temporary-controller 240, operator-computing-device 260, user-computing-device 270, and the like. Wireless-router 250 may be configured for facilitating receiving and transmission of communications between user-transmitter 201, entry-sensor 206, washer 210, soap-dispenser 221, camera 215, hand-dryer 226, at least one server 231, temporary-controller 240, operator-computing-device 260, user-computing-device 270, and the like. In some embodiments, wireless-router 250 may comprise a modem. The modem may be configured for communicating with WAN 801 (e.g. the internet) and/or the LAN.

In some embodiments, WAN 801 is merely a network that may separate at least one server 231 from various target devices and/or hand-washing-compliance area 280, wherein various target devices may be located. In some exemplary embodiments, temporary-controller 240 may be located onsite, but outside of hand-washing-compliance area 280. In some embodiments, at least one server 231 may be located offsite, i.e. remotely from hand-washing-compliance area 280 and from temporary-controller 240, in which case various communications, between at least one server 231 and onsite target devices, may transverse WAN 801. In some embodiments, at least one server 231 may be located onsite but outside of hand-washing-compliance area 280, in which case various communications, between at least one server 231 and onsite target devices, may transverse the LAN.

In some embodiments, operator-computing-device 260 may be selected from the group comprising: a laptop, a smartphone, a tablet computing device, a desktop computer, a server, including at least one server 231. In some embodiments, operator-computing-device 260 may be at least one server 231, e.g. as a laptop or desktop computer. The operator may use operator-computing-device 260 to interact with one or more of at least one server 231, temporary-controller 240, user-transmitter 201, entry-sensor 206, washer 210, camera 215, soap-dispenser 221, hand-dryer 226, wireless-router 250, user-computing-device 270, and the like.

In some embodiments, user-computing-device 270 may be selected from the group comprising: a laptop, a smartphone, a tablet computing device, a desktop computer, a server (but not at least one server 231), and the like. User 950 may use user-computing-device 270 to interact with one or more of at least one server 231, temporary-controller 240, user-transmitter 201, entry-sensor 206, washer 210, camera 215, soap-dispenser 221, hand-dryer 226, wireless-router 250, operator-computing-device 260, and the like.

In some embodiments, user 950 interacting with system 200 and/or method 100 via user-computing-device 270 may be for purposes of viewing reports, notifications, and log entries. In some embodiments, user 950 interacting with system 200 and/or method 100 via user-computing-device 270 may be for purposes of submitting disputes and/or noting a possible need for maintenance.

FIG. 3 may depict exemplary subcomponents of at least one server 231 in a block diagram format. This block diagram may also depict how the subcomponents of temporary-controller 240 may be structured.

In some embodiments, at least one server 231 may comprise: a processor 332, memory 333, network-adapter 334, and a server-power-source 335. Memory 333 may non-transitorily store executable software and user-hand-washing-logs 107 (as one or more databases). Processor 332 may control outputs directed to network-adapter 334 for communication to one or more target devices per instructions contained within the executable software for handling various inputs received via network-adapter 334. Network-adapter 334 may facilitate communications across WAN 801 (e.g. the internet) and/or the LAN with target devices. In some embodiments, the target devices may be selected from one or more of the group comprising, user-transmitter 201, entry-sensor 206, washer 210, camera 215, soap-dispenser 221, hand-dryer 226, temporary-controller 240, wireless-router 250, operator-computing-device 260, user-computing-device 270, and the like. The server-power-source provides electrical power to processor 332, memory 333, and network-adapter 334.

In some embodiments, temporary-controller 240 may temporarily replace at least one server 231, act as a substitute for communications to and from at least one server 231, act a temporary data cache, act as a backup device which may control the various exemplary steps of method 100 for when communication with at least server 231 may be temporarily impaired or otherwise unavailable. Communicating with at least one server may not be possible if there may be an interruption in internet connectivity or problems in bandwidth. Temporary-controller may be a standalone device. In some embodiments, temporary-controller may be located within or outside of hand-washing-compliance-area 280. In some embodiments, temporary-controller 240 may be incorporated within (e.g. integral with) entry-sensor 206, washer 210, soap-dispenser 221, camera 215, hand-dryer 226, wireless router 250, or operator-computing-device 260.

In some embodiments, temporary-controller 240 may be in wireless communication with one or more of the group comprising: user-transmitter 201, entry-sensor 206, washer 210, soap-dispenser 221, camera 215, at least one server 231 via an intermediary network (such as WAN 801 and/or the LAN), hand-dryer 226, operator-computing-device 260, user-computing-device 270, wireless-router 250, and the like.

In some embodiments, temporary-controller 240 may comprise a controller-processor, a controller-memory, a controller-network-adapter, and a controller-power-source. The controller-memory may non-transitorily store executable controller-software, hand-washing-cycle 108 entries, and user-hand-washing-logs 107. The controller-processor may control outputs directed to the controller-network-adapter for communication to one or more target devices per instructions contained within the executable controller-software for handling various inputs received via the controller-network-adapter. The controller-network-adapter may facilitate communications across WAN 801 (e.g. the internet) and/or the LAN with the target devices. In some embodiments, the target devices may be selected from one or more of the group comprising: user-transmitter 201, entry-sensor 206, washer 210, soap-dispenser 221, camera 215, at least one server 231 via an intermediary network (such as WAN 801 and/or the LAN), hand-dryer 226, operator-computing-device 260, user-computing-device 270, wireless-router 250, and the like. The controller-power-source may provide electrical power to the controller-processor, the controller-memory, and controller-network-adapter.

In some embodiments, the executable software (software) may comprise server-software and controller-software. The server-software may be non-transitorily stored within memory 333. The server-software may control how processor 332 processes inputs received from one or more target devices to generate outputs back to the one or more target devices. The controller-software may be non-transitorily stored within the controller-memory of temporary-controller 240. The controller-software may control how the controller-processor processes inputs received from one or more target devices to generate outputs back to the one or more target devices.

In some embodiments, the server-software may comprise an operator-graphical-user-interface (operator-GUI). The operator-GUI may be configured to permit the operator to interact with server-software and/or the controller-software. In some embodiments, the operator-GUI may be accessed by the operator via operator-computing-device 260. Operator-GUI may be accessed on operator-computing-device 260 via a web browser application and/or as a downloaded application (e.g. as a mobile app). In the case of a mobile app embodiment, a version of the server-software and/or the controller software may non-transitorily reside in memory associated with operator-computing-device 260.

In some embodiments, the server-software and/or the controller-software may comprise a user-graphical-user-interface (user-GUI). The user-GUI may be configured to permit the user to interact with the server-software and/or the controller-software. In some embodiments, the user-GUI may be accessed by user via user-computing-device 270. User-GUI may be accessed on user-computing-device via a web browser application and/or as a downloaded application (e.g. as a mobile app). In the case of a mobile app embodiment, a version of the server-software and/or the controller software may non-transitorily reside in memory associated with user-computing-device 270.

Figure 4:
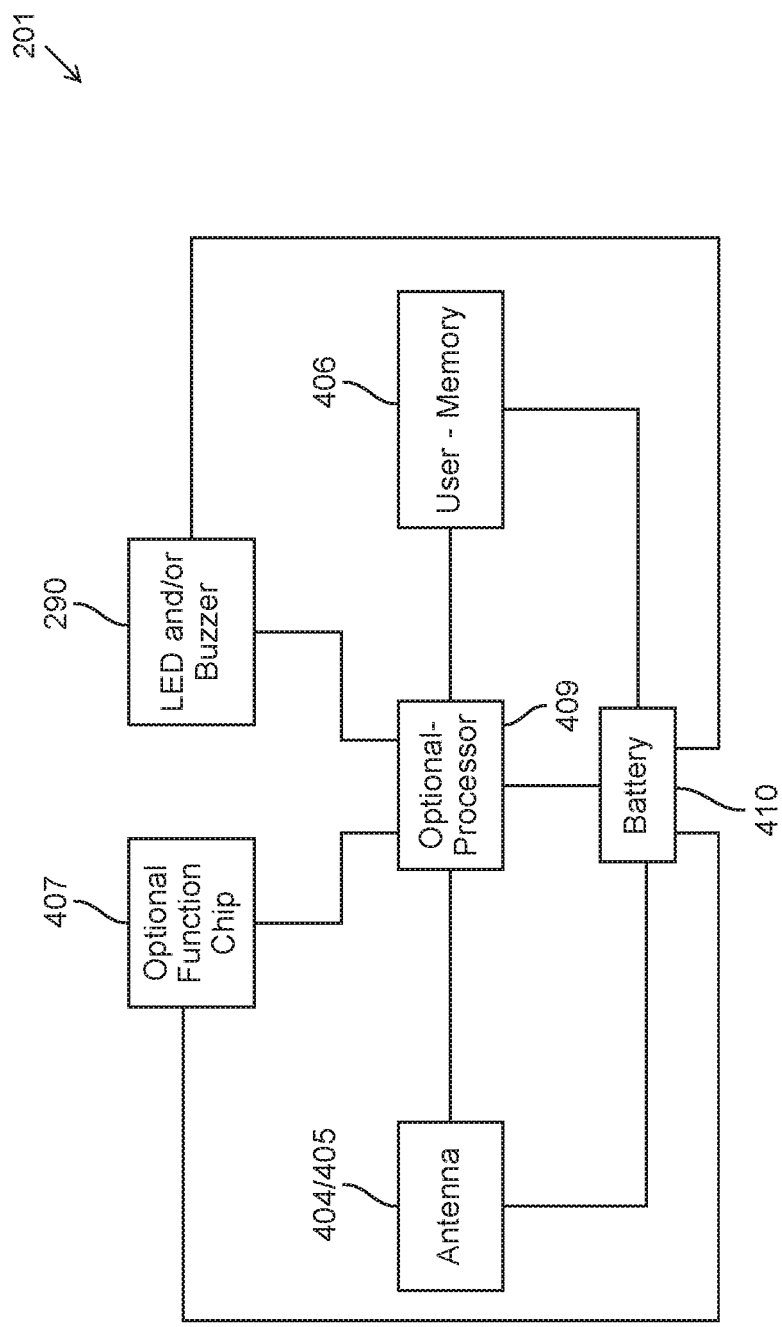
FIG. 4 may depict an exemplary embodiment of subcomponents of the user-transmitter in a block diagram format.

FIG. 4 may depict an exemplary embodiment of subcomponents of user-transmitter 201. In some embodiments, user-transmitter 201 may comprise may comprise: wrist-band 202 or identification-card 203 (see e.g., FIG. 4(a)), wireless-transmitter 404, wireless-receiver 405, and user-memory 406. Wrist-band 202 or identification-card 203 may be the structure that wireless-transmitter 404, wireless-receiver 405, and user-memory 406 may be housed within. In some embodiments, wireless-transmitter 404 and/or wireless-receiver 405 may be a wireless antenna of user-transmitter 201. In active embodiments, user-transmitter 201 may also comprise a power source such as a battery, which may be rechargeable in some embodiments. In passive embodiments, user-transmitter 201 may receive power from other target devices which are sufficiently close to user-transmitter 201.

FIG. 5 may depict an exemplary embodiment of camera 215. In some embodiments, camera 215 may be a stereoscopic camera capable of seeing (observing and/or viewing) in 3D (three dimensions). That is, camera 215 may be able to calculate depth and volume of various objects within camera 215 field of view. Camera 215 may comprise a light projector (emitter) and light receiving sensor (receiver). In some embodiments, the light may be laser light. In further embodiments, the laser light may be infrared (IR) laser light. In such embodiments, the light projector may be projecting IR laser light into a field of view of camera 215. Such projected laser light may reflect off of various objects within the field of view and may then be received by the light receiver (sensor). The light receiver may comprise a monochrome CMOS (complimentary metal-oxide semiconductor) sensor for detecting the reflected IR laser light. By analyzing the received reflected IR laser light and a time of flight for how long it may take the reflected IR laser light to be received by the light receiver (sensor), the software may generate an accurate and precise 3D map of the field of view. Such time of flight 3D depth tracking and mapping technology may be tuned for operation at distances of 1.5 meters or less from the objects being measured to camera 215. Continual projections of such IR laser light and continual receipt of reflected IR laser light may enable camera 215 to see depth and near real-time changes (i.e. movement) in the field of view. Additionally, use of IR light may allow such 3D mapping and motion tracking to operate with or without a presence of visible light.

In some embodiments, camera 215 may comprise digital-optics (i.e. lenses) which may recognize facial features, appendage (limb) anatomy, and hand and finger (digit) anatomy. For example, and without limiting the scope of the present invention, camera's 215 digital-optics may recognize numerosity of shapes and/or length (size) of shapes. For example, camera's 215 digital-optics may recognize how many limbs and/or hands and/or digits may be within the field of view. For example, camera's 215 digital-optics may be able to determine a length of an arm within the field of view. In some embodiments, the digital-optics may comprise digital lenses, such as RBG (red blue green) video capability, as well as the light projector and light receiver (sensor). Camera's 215 digital-optics may recognize if user 950 may be missing fingers, thumbs, hands, or limbs. Camera's 215 digital-optics may recognize thumbs from fingers and fingers from thumbs, and where each finger and thumb should be in relation to each hand.

With respect to user 950 hands, Camera's 215 digital-optics may recognize not only the number of hands (one, two, or none), but may also be able to differentiate a palm side (palmar) of the hands from an opposing dorsal side of the hands.

With respect to user 950 hands, camera's 215 digital-optics may recognize if the palms of two hands are touching and rubbing against each other. Camera's 215 digital-optics may recognize where the hands may be located in 3D space. Camera's 215 digital-optics may be able to differentiate between palms in physical contact and rubbing; from two dorsal sides of the hands in physical contact and rubbing.

In an exemplary embodiment, camera 215 is not comparing digital 2D (two dimensional) images of hands for an output decision. Rather, method 100 and/or system 200 may be watching for, in 3D, whether palms may be coming together, to make a decision on proper or improper hand washing. Method 100, via the software, may be comparing viewed shapes and 3D positions of such viewed shapes against a 3D model of an ideal set of shapes and positions of the pattern recognition algorithm.

In exemplary embodiments, camera 215 may also comprise an infrared (IR) camera or other equivalent thermal sensor. In such embodiments, observing heat emissions from running water and/or from the surface of hands may aid in determining if proper hand washing has occurred or may be occurring. With IR camera functionality proper water temperature use may be verified.

In some embodiments, observed temperature ranges may be assigned different colors for display purposes. For example, and without limiting the scope of the present invention, hot may be assigned to red, warm assigned may be assigned to yellow, and cold may be assigned to blue. With IR camera functionality, verifying actual use of water during pre-rinse and/or during washing may be made easier and more reliable because hot water (but not dangerously hot) over warm hands may provide a useful color contrast; and/or cold water over warm hands may also provide a useful color contrast as picked up by the IR camera.

Including IR camera functionality makes it much more difficult for user 950 to cheat method 100 and/or system 200. For example, with IR camera functionality, method 100 and/or system 200 may be able to differentiate between artificial hands and living humans hands, because living human hands will often have a different surface temperature profile than that of artificial hands.

With respect to user 950 facial recognition, camera's 215 digital-optics may recognize and separate employees from nonemployees to enable user 950 identification. Camera's 215 digital-optics may recognize and separate those users 950 who must adhere to proper hand washing from those who do not. In some embodiments, such recognition and differentiation, via camera 215, may be by facial feature recognition. Specific user 950 anatomical features, such as limb, hand, and digit morphology (e.g. number and size) may also be used to augment recognition and/or identification of various users 950. Such user 950 identification by facial feature recognition and/or by limb, hand and digit morphology may make use of identification via user-transmitter 201 obsolete or redundant. In some embodiments, redundancies may be exemplary to provide backup and as a means to confirm primary identification methods, such as facial feature recognition.

In some embodiments, the light projector and light receiver may also be used to aid in user 950 identification. In such embodiments, special and/or unique patterns may be seen by reflected received IR laser light. Such special and/or unique patterns may be located on exterior surfaces of user-transmitter 201, uniforms, clothing, clothing accessories (e.g. belts), and/or user 950 skin, i.e. in the form of a tattoo. Such special and/or unique patterns may be predominantly visible under IR light. Such special and/or unique patterns may be unique to each specific user 950. Use of such special and/or unique patterns may be in addition to using facial feature recognition; limb, hand, and digit morphology observation; and/or identification of user 950 via user-transmitter 201.

In some embodiments, camera 215 may also comprise one or more microphones. Such microphones may also be located in washer 210, soap-dispenser 221, and/or hand-dryer 226. Such microphone may be configured to sense various sounds emanating within hand-washing-compliance-area 280, such as a sound of running water, a sound of soap being dispensed, and a sound of hands being dried. Use of such microphones may increase the reliability of method 100 and/or system 200. In some embodiments, the one or more microphones may be arranged in an array of three or more microphones. Such an array of microphones may aid in differentiating human sounds from non-human sounds and in a direction of sounds.

In some embodiments, camera 215 may comprise digital-optics (as discussed above), a camera-receiver, a camera-transmitter, a camera-power-source, a camera-memory, a camera-processor, and a feedback-means 290 for providing feedback-signal 180 and/or completion-feedback-signal 170.

In some embodiments, the digital-optics may comprise at least one adjustable lens, at least one light projector, at least one light receiver (sensor), and the like. In some embodiments, at least one adjustable lens may be configured for capturing images of objects within camera's 215 field of view in red, green, and blue colors. In some embodiments, the digital-optics of camera 215 may also comprise thermal-imaging-optics, i.e. the IR camera. In some embodiments, the digital-optics may comprise camera-software (i.e. camera-firmware). The camera-software may instruct the camera-processor how to process images received (i.e. observed and/or viewed) by the at least one adjustable lens. The camera-software may be non-transitorily stored within the camera-memory. Together, the camera-software, the camera-processor, the at least one adjustable lens, and the camera-memory may permit camera 215 to capture (view, observe), record, and recognize: (1) facial features; (2) limb, hand, and digit morphology; (3) user 950 gestures, including hand-gestures; (4) stereoscopic events (motion) within three-dimensional (3D) space of camera's 215 field of view; (5) thermal images, e.g. of warm or cold water; and the like.

In some embodiments, the camera-receiver may be configured to receive transmissions from at least one server 231, temporary-controller 240, user-transmitter 201, entry-sensor 206, washer 210, soap-dispenser 221, hand-dryer 226, operator-computing-device 260, user-computing device 270, and the like.

In some embodiments, the camera-transmitter may be configured to wirelessly transmit a first-recording 111, a second-recording 112, a third-recording 113, a fourth-recording 114, and other recordings. First-recording 111, second-recording 112, third-recording 113 and any other recording from camera 215 may be transmitted to temporary-controller 240 and/or to at least one server 231.

In some embodiments, the camera-power-source may be configured to provide electrical power to: the digital-optics, the camera-receiver, the camera-transmitter, the camera-memory, the camera-processor, the means for providing feedback-signal 180 and/or completion-feedback-signal 170.

In some embodiments, user 950 initiating each phase and/or step may occur by user 950 making appropriate hand-gestures at appropriate locations (e.g. within hand-washing-compliance-area 280). Camera 215 may facilitate hand-gesture recognition by recognizing various defined and appropriate hand-gestures 115 (e.g. defined-hand-gestures 116, defined-pre-rinse-gestures 117, defined-soaping-gestures 118, defined-washing-gestures 119, and/or defined-drying-gestures 120). Camera 215 may also recognize whether the appropriate hand-gesture may be occurring in an appropriate three dimensional location.

For example, and without limiting the scope of the present invention, user 950 making defined-washing-gestures 119 below a faucet of washer 210, may be recorded by camera 215 as both an appropriate hand-gesture and as occurring in an appropriate three dimensional location, such that camera 215 may cause a signal received by washer 210 for washer 210 to turn on the running of water. Likewise, when user 950 may remove hands from this appropriate three dimensional location, camera 215 may recognize this and cause another signal received by washer 210 for washer 210 to turn the water off.

For example, and without limiting the scope of the present invention, user 950 making defined-soaping-gestures 118 below soap-dispenser 221, may be recorded by camera 215 as both an appropriate hand-gesture and as occurring in a recognized three dimensional location, such that camera 215 may cause a signal received by soap-dispenser 221 to dispense soap from soap-dispenser 221. Likewise, when user 950 may remove hands from this appropriate three dimensional location, camera 215 may recognize this and cause another signal to be sent to soap-dispenser 221 such that soap may no longer be dispensed.

For example, and without limiting the scope of the present invention, user 950 making defined-drying-gestures 120 within a proximity of hand-dryer 226, may be recorded by camera 215 as both an appropriate hand-gesture and as occurring in a recognized three dimensional location, such that user 950 may cause a signal to be sent to hand-dryer 226 to either blow air or to provide a towel. Likewise, when user 950 may remove hands from this appropriate three dimensional location, camera 215 may recognize this and cause another signal to be sent to hand-dryer 226 such that air blowing ceases or no more towels may be provided.

In some embodiments, user 950 may initiate a start to any particular phase by user 950 bringing user-transmitter 201 within sufficient proximity to entry-sensor 206, washer 210, soap-dispenser 221, and/or hand-dryer 226. In some embodiments, user 950 may initiate a start to any particular phase by user 950 by a combination of bringing user-transmitter 201 within sufficient proximity to a particular component and/or by performing appropriate hand-gestures 115 at appropriate locations.

In some embodiments, privacy concerns of a given user 950 may be mitigated by appropriate placement (e.g. mounting) of camera 215 within a given hand-washing-compliance-area 280, such that camera's 215 field of view may be appropriately restricted. Additionally, in some embodiments, privacy concerns of a given user 950 may be mitigated by camera 215 being configured such that the field of view may be restricted to washer 210, soap-dispenser 221, and/or hand-dryer 226. Additionally, in some embodiments, privacy concerns of a given user 950 may be mitigated by recordings of camera 215 being restricted to recognized gestures, recognized gestures within an appropriate three dimensional space, and/or thermal images.

Additionally, in some exemplary embodiments, privacy concerns of a given user 950 may be mitigated by camera 215 not making any recordings. In such embodiments, camera 215 may only be capturing (viewing and/or observing) hand and digit shapes and position in 3D information for use against an ideal set of shapes and positions of the pattern recognition algorithm. That is, in such embodiments, camera 215 may not be capturing images of hands that may be readily deciphered by a human reviewing and/or observing an output from camera 215. In such embodiments, camera 215 may be essentially acting as a sensor that may detect shapes and positioning of hands and digits of user 950. Technically, in such embodiments, camera 215 may not even be detecting hands and digits; but rather, camera 215 may be detecting objects within its 3D field of view, i.e. shapes and positions of objects may be detected by camera 215. Such detected shapes and positions of objects, in near real-time, may then be run through the pattern recognition algorithm. The pattern recognition algorithm may ask if those observed shapes and positions of observed objects sufficiently matches the ideal set of shapes and positions. The ideal set of shapes and positions may correspond to ideal hand washing of an imaginary user 950 conducting ideal hand washing through the various hand washing phases. After comparison, the pattern recognition algorithm may cause logging of compliant log entry or a non-compliant log entry. The pattern recognition algorithm may be a subcomponent of the software and may be non-transitorily stored within memory 333 of at least one server 231, or corresponding controller-memory of temporary-controller 240.

A method and system for user hand washing compliance has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A system for user hand washing compliance comprising: a user-transmitter, wherein the user-transmitter is integral to a wrist-band or an identification-card, wherein the user-transmitter is maintained with a user, wherein the user-transmitter comprises a wireless-transmitter, wherein the wireless-transmitter wirelessly transmits a first-wireless-transmission;

an entry-sensor, wherein the entry-sensor is located at an access point to a hand-washing-compliance-area, wherein the entry-sensor comprises a sensor-receiver, a sensor-transmitter, and a sensor-power-source; wherein the sensor-receiver is configured to receive the first-wireless-transmission; wherein the sensor-transmitter is configured to wirelessly transmit a second-wireless-transmission; and wherein the sensor-power-source is configured to provide electrical power to the sensor-receiver and to the sensor-transmitter;

a washer, wherein the washer comprises a means for dispensing water, a washer-receiver, a washer-transmitter, and a washer-power-source; wherein the washer-receiver is configured to receive transmissions from at least one server and/or the user- transmitter; wherein the washer-transmitter is configured to wirelessly transmit a third-wireless- transmission; and wherein the washer-power-source is configured to provide electrical power to the washer-receiver and to the washer-transmitter;

a soap-dispenser, wherein the soap-dispenser comprises a means for dispensing soap, a soap-dispenser-receiver, a soap-dispenser-transmitter, and a soap-dispenser-power- source; wherein the soap-dispenser-receiver is configured to receive transmissions from the at least one server and/or the user-transmitter;

wherein the soap-dispenser-transmitter is configured to wirelessly transmit a fourth-wireless-transmission; and wherein the soap- dispenser-power-source is configured to provide electrical power to the soap-dispenser-receiver and to the soap-dispenser-transmitter;

a camera, wherein the camera comprises digital-optics, a camera-receiver, a camera-transmitter, and a camera-power-source; wherein the camera-receiver is configured to receive transmissions from the at least one server and/or the user-transmitter; wherein the camera-transmitter is configured to wirelessly transmit a first-recording, a-second recording, and, a third recording; and wherein the camera-power-source is configured to provide electrical power to the digital-optics, the camera-receiver and to the camera-transmitter; and the at least one server, wherein the at least one server comprises: a processor, memory, network-adapter, and a server-power-source, wherein the memory non-transitorily stores executable software and user-hand-washing-logs, wherein the processor controls outputs directed to the network-adapter for communication to one or more target devices per instructions contained within the executable software for handling various inputs received via the network-adapter, wherein the network-adapter facilitates communications across a wide- area-network and/or a local-area-network with target devices, wherein the server-power-source provides electrical power to the processor, the memory, and network-adapter;

wherein, receipt of the first-wireless-transmission by the sensor-entry initiates transmission of the second-wireless-transmission by the sensor-entry;

wherein, the second-wireless-transmission comprises information logging initiation of a hand-washing-cycle in the user-hand-washing-log, wherein the hand-washing- cycle comprises at least one log entry pertaining to a given user's interactions with the system, wherein the user-hand-washing-log is a database;

wherein the third-wireless-transmission comprises information: noting the washer is on with running water, noting the washer is off with no running water, noting completion of a defined-first-duration, and/or noting completion of a defined-third-duration;

wherein the fourth-wireless-transmission comprises information: noting the soap-dispenser is on and activated, noting the soap-dispenser is off, and/or completion of a defined- second-duration;

wherein the first-recording is of the user wetting hands under water running from the washer during the defined-first-duration;

wherein the second-recording is of the user receiving soap from the soap-dispenser;

wherein the third-recording is of the user washing and subsequently rinsing the soap from the user's hands during the defined-third-duration;

wherein the at least one server transmits a hand-washing-cycle-completion-signal to one or more of the user-transmitter, the entry-sensor, the washer, the camera, and/or the soap-dispenser; wherein receipt of the hand-washing-cycle-completion-signal results in a completion-feedback-signal being broadcast to the user.

* * * * *